United States Patent
Alabi et al.

(10) Patent No.: US 12,005,451 B2
(45) Date of Patent: Jun. 11, 2024

(54) SYSTEM AND METHOD FOR OIL CONDITION MONITORING

(71) Applicant: RAB MICROFLUIDICS RESEARCH AND DEVELOPMENT COMPANY LIMITED, Aberdeen (GB)

(72) Inventors: Oluwarotimi Alabi, Aberdeen (GB); Surakat Kudehunbu, Aberdeen (GB); Barry James Warden, Aberdeen (GB); Stephen McIntosh, Aberdeen (GB)

(73) Assignee: RAB Microfluidics Research and Development Company Limited, Arberdeen (GB)

( * ) Notice: Subject to any disclaimer, the term of this patent is extended or adjusted under 35 U.S.C. 154(b) by 660 days.

(21) Appl. No.: 17/256,348

(22) PCT Filed: Jun. 28, 2019

(86) PCT No.: PCT/GB2019/051846
§ 371 (c)(1),
(2) Date: Dec. 28, 2020

(87) PCT Pub. No.: WO2020/002946
PCT Pub. Date: Jan. 2, 2020

(65) Prior Publication Data
US 2021/0260585 A1    Aug. 26, 2021

(30) Foreign Application Priority Data

Jun. 28, 2018 (GB) .................................... 1810589

(51) Int. Cl.
*F01M 11/10* (2006.01)
*B01L 3/00* (2006.01)
(Continued)

(52) U.S. Cl.
CPC ........ *B01L 3/502753* (2013.01); *F01M 11/10* (2013.01); *G01J 3/10* (2013.01);
(Continued)

(58) Field of Classification Search
CPC .................................. G01J 3/10; F01M 11/10
See application file for complete search history.

(56) References Cited

U.S. PATENT DOCUMENTS

| | | | |
|---|---|---|---|
| 2008/0181821 A1* | 7/2008 | Jung ................. | B01L 3/502753 422/68.1 |
| 2014/0008307 A1* | 1/2014 | Guldiken .......... | B01L 3/502761 422/502 |

(Continued)

OTHER PUBLICATIONS

Alabi, O.O., Bowden, S.A. and Parnell, J (2014) 'Simultaneous and rapid asphaltene and TAN determination for heavy petroleum using an H-cell', Analytical Methods, 6(11), pp. 3651-3661.

(Continued)

*Primary Examiner* — Jamel E Williams
(74) *Attorney, Agent, or Firm* — FisherBroyles, LLP

(57) ABSTRACT

The invention provides a microfluidic system for monitoring the condition of lubricating oil. The microfluidic system comprises a microfluidic device with at least one microchannel (40) configured to allow a sample of lubricating oil (52a) to pass therethrough as a laminar flow. The device has at least one separating device (41) configured to selectively separate at least one component (54b) from the lubricating oil (52a) in the fluid flow. The microfluidic system also comprises a detector device (20, 22) configured to detect the presence and/or measure at least one property of the at least one component passing through the microfluidic device after separation in the microchannel (40).

25 Claims, 15 Drawing Sheets

(51) Int. Cl.
*G01J 3/10* (2006.01)
*G01N 33/28* (2006.01)

(52) U.S. Cl.
CPC ..... *G01N 33/2858* (2013.01); *G01N 33/2888* (2013.01); *B01L 2300/0681* (2013.01); *F01M 2011/1413* (2013.01); *F01M 2011/144* (2013.01)

(56) References Cited

U.S. PATENT DOCUMENTS

2014/0242682 A1* 8/2014 Curry ............... G01N 33/574
    435/287.2
2015/0209782 A1* 7/2015 Mostowfi ............ G01N 21/05
    422/503

OTHER PUBLICATIONS

ASTM D721-06 Standard Test Method for Oil Content of Petroleum Waxes, American Society for Testing and Materials, West Conshohocken, PA, 2011.
Aucelio, R.Q., de Souza, R.M., de Campus, R.C., Miekeley, N., and Porto da Silveira, C.L. (2007). The determination of trace metals in lubricating oils by atomic spectrometry. Spectrochimica Acta Part B, 62(9), 952-961.
Barnes J, Hengeveld J, Foster S, Schasfoort T, Scheele R (2004) Oil stress investigations in Shell's medium speed laboratory engine. CIMAC Congress, Kyoto.
Bowden, S.A., Monaghan, p. B., Wilson, R., Parnell, J. and Cooper, J.M. (2006) 'The liquid-liquid diffusive extraction of hydrocarbons from a North Sea oil using a microfluidic format', Lab on a Chip, 6(6), pp. 740-743.
Bowden, S.A., Wilson, R., Parnell, J. and Cooper, J.M. (2009) 'Determination of the asphaltene and carboxylic acid content of a heavy oil using a microfluidic device', Lab on a Chip, 9(6), pp. 828-832.

Brody, J.P. and Yager, P. (1996) 'Low Reynolds No. micro-fluidic devices', Proc. of Solid-State Sensor and Actuator Workshop, Hilton Head, South Carolina pp. 105-108.
Carballo, S., Terán, J., Soto, R.M., Carlosena, A. Andrade, J.M. and Prada, D. (2013). Green approaches to determine metals in lubricating oils by electrothermal atomic absorption spectrometry (ETAAS). Microchemical Journal, 108, 74-80.
Clark RJ, and Fajardo CM. (2012). Assessment of the properties of internal combustion engine lubricants using an onboard sensor. Tribology Transactions, 55, 458-65.
Goncalves, I.M., Murillo, M. and Gonzalez, A.M. (1998). Determination of metals in used lubricating oils by AAS using emulsified samples, Talanta 47, 1033-1042.
Reischman, P.T, and Rafi Jalkian, R (2007) Method for determining asphaltenes contamination in used marine engine ubricants using UV-visible spectroscopy and chemometrics. US Patenet: U.S. Pat. No. 7407809 B2. Exxonmobil Research And EngineeringCompany.
Smiechowski MF, and Lvovich VF. Iridium oxide sensors for acidity and basicity detection in industrial lubricants. Sens Actuators B Chem 2003;96:261-7.
Sutton M, and Stow C. (2004) Preliminary studies of the impact of diesel fuel sulphur on recommended oil service Interval. In: Proceedings of the international conference on sustainable automotive technologies 2004; pp. 131-135.
Toms, A and Toms L. (2010) Oil analysis and condition monitoring. In: Chemistry and Technology of Lubricants, Springer, pp. 459-495.
Zheng, L, Cao, F., Xiu, J., Bai, X., Motto-Ros, V., Gilon, N., Zeng, H. and Yu, J. (2014). On the performance of laser-induced breakdown spectroscopy for direct determination of trace metals in lubricating oils. Spectrochimica Acta Part 3, 99, 1-8.
Zhu, J., Yoon, J. M., He, D., Qu Y. and Bechhoefer, E. (2013). Lubrication Oil Condition Monitoring and Remaining Useful Life Prediction with Particle Filtering. International Journal of Prognostics and Health Management. 20, 1-15.
Zhu, X., Zhong, C. and Zhe, J (2017). Lubricating oil conditioning sensors for online machine health monitoring—A review. Tribology International, 109, 473-484.

* cited by examiner

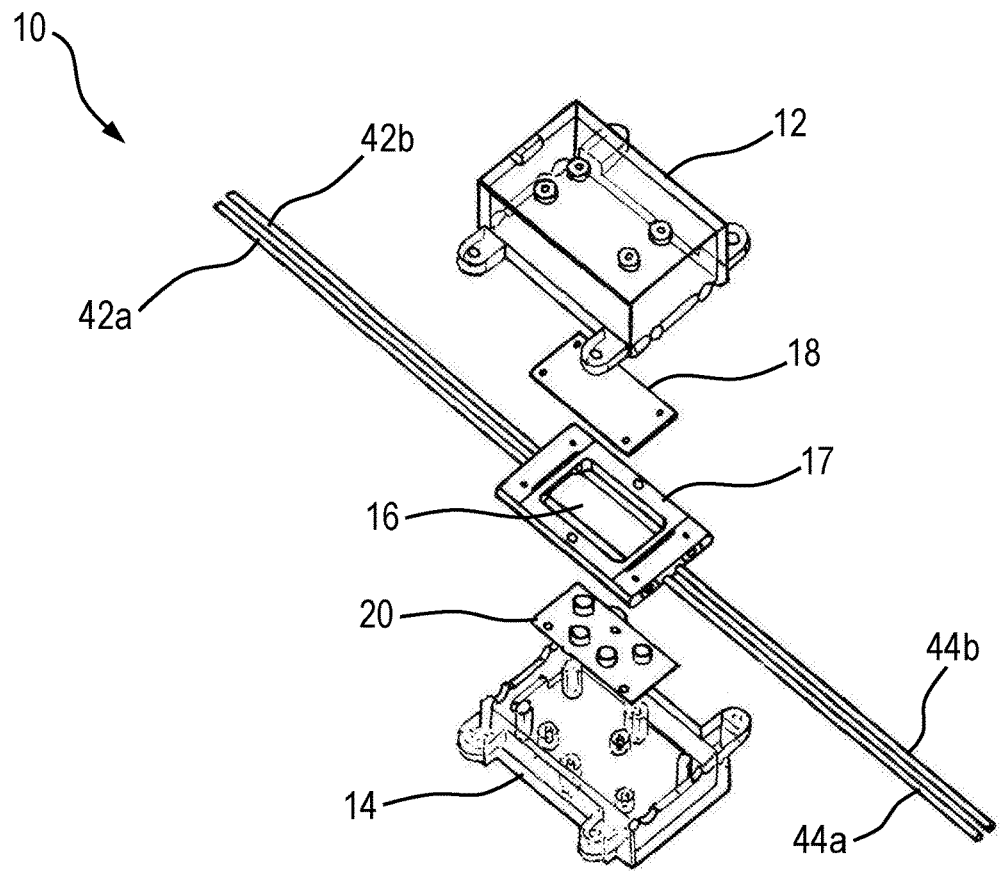
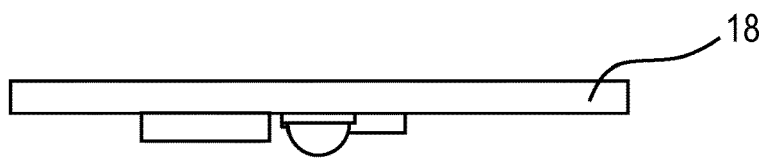
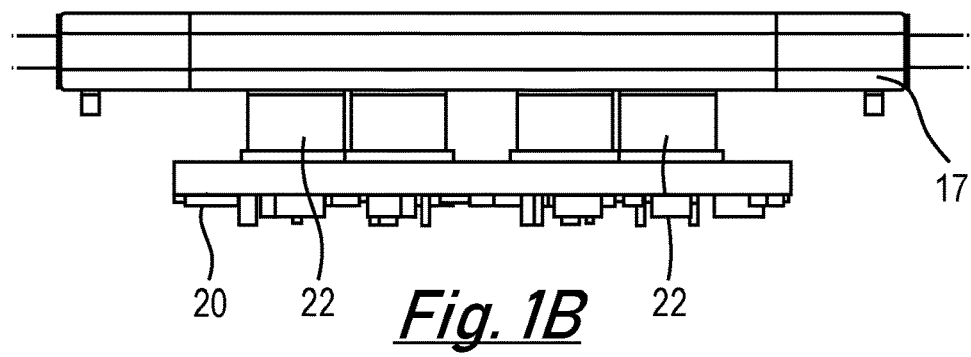
Fig. 1A
Fig. 1B

SYSTEM AND METHOD FOR OIL CONDITION MONITORING

This application is the U.S. National Stage of International Application No. PCT/GB2019/051846, which was filed on Jun. 28, 2019. This application also claims the benefit of the filing date of GB patent application No. 1810589.0, which was filed on Jun. 28, 2018. The contents of both of those applications are hereby incorporated by reference.

The present invention relates to apparatus and methods for use in monitoring oil condition. Aspects of the invention relate to microfluidic apparatus for monitoring the condition of lubricating oil of machinery.

BACKGROUND TO THE INVENTION

Lubricating oils are essential for the operation of machinery and engine components. Under normal operating conditions, moving parts in machinery and engines undergo wear. Lubricating oils are used to minimise such wear in between the moving parts and prolonging the lifespan of the machinery.

Over time the lubricating oils may become contaminated by wear debris due to mechanical erosion, spalling, pitting, fatigue or corrosion of the component or its surfaces. Furthermore, the lubricating oils over time may become degraded by chemical or water infiltration or the chemical composition of the oil may change.

In order to maintain the performance and efficiency of machinery or engines and avoid damage, the quality of the lubricating oil must be monitored for contamination and degradation.

Lubricating oil can be analysed in a laboratory using different techniques such as elemental measurements, particle counting and chromatography. This analysis gives an indication of the health of the machinery and its components. Such Oil Condition Monitoring (OCM) provide a detection of changes in lubricant conditions and provide insight into the condition of the machinery. However, collecting samples, transporting and testing in a laboratory is slow and labour intensive. Consequently analysis may only be preformed quarterly which reduces the ability to pre-empt machine failure.

SUMMARY OF THE INVENTION

It is an object of an aspect of the present invention to obviate or at least mitigate the disadvantages of prior art oil condition monitoring apparatus and methods.

It is an object of an aspect of the present invention to provide a robust, reliable and compact microfluidic apparatus and incorporated chemical and/or physical sensors suitable for monitoring the health and condition of a piece of machinery by analysing the products of wear, degradation and contamination in lubricating oil.

It is another object of an aspect of the present invention to provide a robust, reliable and compact microfluidic apparatus and incorporated chemical and/or physical sensors suitable for monitoring the condition of lubricating oil condition and detecting of analytes indicative of wear.

It is a further object of an aspect of the present invention to provide a microfluidic chip which is capable of improving the performance of a microfluidic apparatus in which the microfluidic chip is deployed.

It is another object of the invention to provide a method of detecting analytes and/or parameters of analytes in lubricating oil which may be indicative of machinery wear or corrosion and allow high-throughput oil analysis.

Further aims of the invention will become apparent from the following description.

According to a first aspect of the invention, there is provided a microfluidic system for monitoring the condition of lubricating oil comprising:

a microfluidic device comprising at least one microchannel configured to allow a sample of lubricating oil to pass there through; and a detector device configured to detect the presence and/or measure the level of at least one analyte in the sample.

Preferably the at least one analyte may be at least one component of the lubricating oil.

The microfluidic device may comprise at least one separation device configured to selectively separate or extract at least one component of the lubricating oil from the fluid flow. The at least one separation device may be selected from the group comprising a diffusion extractor, a magnet and/or a metal-based sulphur removal device.

The separation device may be configured for diffusive separation, liquid-liquid separation and/or magnetic separation. Preferably the at least one microchannel forms a diffusion extractor. The diffusion extractor may be a H-filter.

The microchannel may be configured to allow a sample of lubricating oil to pass there through as a laminar flow.

The diffusion extractor may comprise a plurality of inlets and outlets. The diffusion extractor may comprise a first inlet and a second inlet. The first inlet may be configured to receive an oil sample. The first inlet may be in fluid communication with lubricating oil from a piece of machinery to be tested.

The diffusion extractor may be configured to selectively extract components in lubricating oil in the microfluidic channel through diffusive extraction with a solvent. Flow in the microchannel may permit liquid-liquid diffusive separation between otherwise miscible non-aqueous fluids. The extracted components may be low molecular weight components. The solvent and the lubricating oil sample may be coflowing in the microchannel at ambient temperature where both solvent and oil phases are in contact which each other. The components may diffuse from the oil phase into a solvent phase in the diffusion extractor. The diffusion extractor may enable a controlled interaction between the laminar oil phase flow and the solvent phase flow. Preferably there is no turbulence associated with mixing between the phases.

The second inlet may be configured to receive a solvent. The second inlet may be in fluid communication with a pump and/or fluid system comprising solvent or a solvent reservoir.

Preferably the diffusion extractor comprises a diffusion channel. Preferably the first inlet and second inlet are in fluid communication with the diffusion channel.

The diffusion extractor may comprise a first outlet and a second outlet. The first outlet and a second outlet may be in fluid communication with the diffusion channel. The first and second inlets, diffusion channel and first and second outlet may have a generally H-shaped geometry or profile.

The first outlet and/or second outlets may be in fluid communication with a waste reservoir. The first outlet may be in fluid communication with an oil sample waste reservoir. The second outlet may be in fluid communication with a solvent waste reservoir.

The diffusion extractor may be configured to allow an analyte present in an oil sample in the first inlet to diffuse from the oil sample into the solvent in the diffusion channel and pass out through the second outlet into the solvent waste reservoir.

The diffusion extractor may be configured to allow an analyte present in an oil sample in the first inlet to remain in the oil sample and at least one other component of the oil sample to diffuse into the solvent in the diffusion channel and pass out through the second outlet into the solvent waste reservoir.

The diffusion extractor may be configured to selectively extract compounds of interest, e.g. carboxylic acid or low molecular weight fraction (non-asphaltene fraction) of oil (for asphaltene measurement) which are indicative of or result from lubricating oil contaminates.

The at least one analyte may be selected from the group consisting of metals, carboxylic acid, naphthenic acid, asphaltene, n-alkane insoluble, organic solids, sulphonates and/or sulphur. The diffusion extractor may be configured to diffuse out multiple analytes in the sample.

N-alkane insoluble components may include asphaltene, soot, organic solids and/or wear/abrasion products.

Preferably the carboxylic acids are naphthenic acids. Naphthenic acids may include all carboxylic acids present in crude oil including alicyclic and aromatic acids.

The detection of the presence, absence or measurement of the level of analyte e.g. naphthenic acid, sulphonates, organic solids in the lubricating oil may be indicative of the condition or health of the piece of machinery. The detection of the presence, absence or measurement level of at least one other component of the oil sample may determine the presence, absence or measurement level of analyte in the lubricating oil.

The detector device may be configured to detect the presence and/or measure the modal properties of at least one analyte or at least one component in the sample. Analysis of the modal properties of the at least one analyte or at least one component may be indicative of the condition the machinery lubricating oil. The detector device may be configured to measure changes in extracting solvents, changes in corrosion of chemical indicators, measure spalled metals from machinery components. The detector device may measure chemical composition of lubricating oil or a component of the lubricating oil. The detector device may measure changes in chemical composition of lubricating oil or a component thereof as a function of time.

The detector device may be configured to detect of the presence, absence or a measurement of the level of at least one property of at least one analyte. The detector device may be configured to detect of the presence, absence or a measurement of the level of at least one property of at least one component in the oil.

The property may include insolubility, solubility, dielectric properties, non-conductive oxides, and reactivity with metals. The measurements may include UV absorption, capacitance, voltage, IR oxide, differences in UV-VIS absorption spectra, reaction with metals, acid or water soluble-coating.

The detector device may be located in, on, above, below or adjacent to the at least one microchannel.

The detector device may be located in, on, above, below or adjacent to first inlet, second inlet, diffusion channel, first outlet and/or second outlet. The detector device may in fluid communication with the first inlet, second inlet, diffusion channel, first outlet and/or second outlet.

The microchannel may comprise at least one observation or interrogation site. The at least one observation site may be located in the first inlet, second inlet, diffusion channel, first outlet and/or second outlet. The at least one observation site may be located in tubing connected to the first inlet, second inlet, diffusion channel, first outlet and/or second outlet The system may comprise a light source. The light source may be selected to provide light in the UV, VIS and/or IR range.

The at least one observation site may be located between a light source and the detector device. The light source and detector may be located at the opposing sides of the at least one observation site. The light source and detector may be positioned such that light passes from the light source through the observation site and onto the detector during use.

The detector device may comprise at least one sensor. The at least one sensor may be selected from the group comprising a spectrometer, camera, Charge Coupled Device (CCD), Complementary Metal Oxide Semi-conductors (CMOS) or another photosensitive device, conductivity sensor, capacitance sensor and/or a metal responsive to a chemical analyte. The at least one sensor may be a spectrometer to sense, measure and/or record a spectrum from the at least one analyte and/or a component of the lubricating oil.

The analyte may be detected by measuring UV-absorption. The analyte may be detected by measuring a difference in UV-Vis, NIR and/or MIR Absorption.

The at least one sensor may be a metal-based chemical indicator or sensor responsive to a chemical compound or analyte in the oil sample wherein the metal undergoes a chemical reaction in the presence of the analyte to produce a signal. A detector may be configured to detect the signal produced by the chemical interaction of the analyte with the metal during use. The at least one sensor may be metal responsive to sulphur or sulphur reactive species. The at least one sensor may be selected from the group comprising copper or silver. The signal may be a marking or tarnishing. i.e. reaction product on the surface of the metal detectable by a camera, microscope and/or other inbuilt sensor including those operating in the infrared or visible spectrum.

The at least one sensor may be an electrical conductivity sensor or an electrical capacitance sensor. The sensor may be located in, on, above, below or adjacent to a microchannel in the microfluidic device. The microchannel may be the first inlet, second inlet, diffusion channel, first outlet and/or second outlet.

The conductivity sensor and/or capacitance sensor may use the magnetic properties of the metal debris in the lubricating oil to separate the metal particles in the oil sample before the conductivity and/or capacitance measurement.

The conductivity sensor may comprise a first electrode, a second electrode and a magnet. The magnet may be in contact with the first electrode. The magnet may attract metal filings or particles to complete an electrical circuit between the first and second electrodes.

The capacitance sensor may comprise two metal plates adjacent to a magnet. The magnet may be attached to the base of the microchannel (on the reverse side) to attract metal filings and increase the sensitivity of capacitance measurements.

The microchannel may comprise at least one magnet located in, on, above, below or adjacent to first inlet, second inlet, diffusion channel, first outlet and/or second outlet to attract metal fragments in the sample.

Preferably the microfluidic device may be a low Reynolds number fluidic apparatus. The microfluidic system may be configured to detect the presence and/or measure the level of at least one analyte or component in the sample in real time.

The microfluidic device may comprise more than one type of separation device configured to extract at least a component of the lubricating oil from the fluid flow. The separation devices may be selected from the group comprising a diffusion extractor, a magnet and/or a metal-based sulphur removal device.

According to a second aspect of the invention, there is provided a microfluidic system for monitoring the health of a piece of machinery by analysing the condition of lubricating oil comprising:
  a microfluidic device comprising at least one microchannel configured to allow a sample of lubricating oil to pass therethrough; and
  a detector device configured to detect the presence and/or measure the level of at least one analyte in the sample.

Preferably the microfluidic device may be a low Reynolds number fluidic apparatus.

Embodiments of the second aspect of the invention may include one or more features of the first aspect of the invention or its embodiments, or vice versa.

According to a third aspect of the invention there is provided a microfluidic device for a microfluidic system, the microfluidic device comprising;
  a microfluidic chip comprising at least one microchannel configured to allow a sample of lubricating oil to pass therethrough.

The microfluidic chip may comprise a plurality of microchannels. The microchannels may be in fluid communication with each other. The microfluidic chip may comprise a first inlet, a second inlet, a diffusion channel, a first exit and a second exit.

The arrangement of the first and second inlets, diffusion channel and first and second outlet may form a diffusion extractor. The diffusion extractor may be a H filter. The first and second inlets, diffusion channel and first and second outlet may have a generally H-shaped geometry or profile.

The first inlet is configured to be connectable to a source of lubricating oil. The second inlet is configured to the connectable to a source of solvent. The solvent may be selected from the group comprising hexane, dichloromethane, toluene, ethanol, Isopropyl Alcohol (IPA), methanol and/or salt liquids.

The diffusion extractor may be dimensioned to allow the at least one analyte or component to diffuse out of the oil sample into a solvent. The diffusion extractor may be dimensioned to allow an analyte or component present in an oil sample in the first inlet to remain in the oil sample and other components of the oil sample to diffuse into the solvent in the diffusion channel and pass out through the second outlet into the solvent waste reservoir.

Preferably the at least one analyte or component is selected from the group consisting of metals, carboxylic acid, naphthenic acid, asphaltene, n-alkane insoluble, organic solids, sulphonates and/or sulphur. The diffusion extractor may be configured to diffuse out multiple analytes in the sample.

The detector may be configured to measure a first component of the oil sample which may be used to infer or determine the presence or measurement level of a desired analyte. The first component may be asphaltene-free fraction (maltene fraction) of the oil and the desired analyte may be asphaltene. The first component may be n-alkane insolubles-free fraction (maltene fraction) of the oil and the desired analyte may be n-alkane insolubles.

The microfluidic chip may comprise at least one sensor located in, on, above, below or adjacent to first inlet, second inlet, diffusion channel, first outlet and/or second outlet. The detector device may in fluid communication with the first inlet, second inlet, diffusion channel, first outlet and/or second outlet.

The at least one sensor may be a chemical sensor and/or a physical sensor. By physical sensor it is meant a sensor capable of measuring a physical property.

The at least one sensor may be selected from the group comprising a spectrometer, camera, Charge Coupled Device (CCD), Complementary Metal Oxide Semi-conductors (CMOS) or another photosensitive device, a conductivity sensor, capacitance sensor and/or a metal responsive to a chemical analyte.

Preferably the microfluidic device may be a low Reynolds number fluidic apparatus.

Embodiments of the second aspect of the invention may include one or more features of the first aspect of the invention or its embodiments, or vice versa.

According to a fourth aspect of the invention, there is provided a method of monitoring the condition of lubricating oil comprising
  providing a microfluidic system comprising:
  a microfluidic device comprising at least one microchannel; and
  a detector device;
  passing a sample of the lubricating oil through the at least one microchannel;
  detecting the presence of and/or measuring the level of at least one desired analyte in the sample.

The least one desired analyte may be at least one component of the lubricating oil. The microfluidic device may comprise a separating device and the method may comprise separating and/or extracting the at least one desired analyte from the lubricating oil. The at least one desired analyte may be detected after or during separation and/or extraction of the analyte from the flow in the microchannel.

The method may comprise detecting the presence of and/or measuring the level of at least one desired analyte by spectrometry, electrical conductivity, electrical capacitance and/or reactivity of the analyte to a chemical and/or optical or nuclear spectrometry.

The method may comprise extracting, separating and/or diffusing the analyte from the sample before detecting the presence of and/or measuring the level of the desired analyte.

The method may comprise extracting, separating and/or diffusing the analyte from the sample in the microchannel.

The method may comprise extracting, separating and/or diffusing the analyte by mass transfer, diffusion, magnetic or electrical attraction or chemical interaction or dielectrophoresis or any other method by which to introduce a gradient force.

The method may comprise taking a reading of the lubricating oil sample before extracting, separating and/or diffusing at least one component of the oil leaving the analyte remaining in the lubricating oil and detecting the presence of the analyte or measuring the level of the analyte by determining the difference in readings from the lubricating oil sample and the readings of the extracted at least one component.

The method may comprise taking at least one measurement of the lubricating oil sample before extracting, separating and/or diffusing at least one component of the oil and comparing with at least one measurement of the sample after the at least one component is extracted.

The method may comprise detecting, measuring and/or recording a spectrum from an analyte. The method may comprise detecting, measuring and/or recording a spectrum from an extracted component of the oil sample. The method may comprise comparing a spectrum from an extracted component of the oil sample with a spectrum of the entire oil sample to detect or measuring a desired analyte.

The method may comprise comparing a spectrum of the sample with a spectrum from an extracted component of the sample.

The method may comprise detecting, measuring and/or recording an electrical capacitance and/or electrical conductivity of an analyte in the oil sample. The method may comprise detecting, measuring and/or recording the chemical response of an analyte in the oil sample to metal sensor or metal reagent.

The method may comprise obtaining a sample of lubricating oil from machinery to determine the health and condition of the piece of machinery.

The at least one analyte or component is selected from the group consisting of metals, carboxylic acid, asphaltene, n-alkane insoluble/organic solids, sulphonates and/or sulphur. The method may detect multiple analyte or component types in the sample.

Preferably the microfluidic device may be a low Reynolds number fluidic apparatus.

Embodiments of the fourth aspect of the invention may include one or more features of the first to third aspects of the invention or their embodiments, or vice versa.

A fifth aspect of the invention therefore relates to a method of monitoring the condition of a piece of machinery by analysing lubricating oil comprising:
  providing a microfluidic system comprising:
  a microfluidic device comprising at least one microchannel; and
  a detector device;
  passing lubricating oil through the at least one microchannel;
  detecting the presence of and/or measuring the level of at least one desired analyte in the sample.

Embodiments of the fifth aspect of the invention may include one or more features of any of the first to fourth aspects of the invention or their embodiments, or vice versa.

According to a sixth aspect of the invention, there is provided a method of detecting the presence and/or level of an analyte in a lubricating oil sample comprising providing a microfluidic system comprising:
  a microfluidic device comprising at least one microchannel; and
  a detector device;
  passing a lubricating oil sample through the at least one microchannel;
  detecting the presence and/or level of at least one desired analyte in the sample.

Embodiments of the sixth aspect of the invention may include one or more features of any of the first to fifth aspects of the invention or their embodiments, or vice versa.

According to a seventh aspect of the invention, there is provided a method of detecting the presence and/or level of a metal analyte in a lubricating oil sample comprising providing a microfluidic system comprising:
  a microfluidic device comprising at least one microchannel; and
  a detector device;
  passing a lubricating oil sample through the at least one microchannel;
  detecting the presence and/or level of the metal analyte in the sample.

The method may comprise attracting the metal analyte to a magnet located in or adjacent to the microchannel. The method may comprise providing at least one electrode to take electrical conductivity readings and/or electrical capacitance readings.

Embodiments of the seventh aspect of the invention may include one or more features of any of the first to sixth aspects of the invention or their embodiments, or vice versa.

According to an eighth aspect of the invention, there is provided a method of detecting the presence and/or level of a carboxylic acid in a lubricating oil sample comprising providing a microfluidic system comprising:
  a microfluidic device comprising at least one microchannel; and
  a detector device;
  passing a lubricating oil sample through the at least one microchannel;
  detecting the presence and/or level of carboxylic acid in the sample.

The method may comprise extracting, separating and/or diffusing the carboxylic acid from the oil sample before detecting the presence of and/or measuring the level of the carboxylic acid.

The method may comprise passing the sample through a diffusion extractor. The diffusion extractor may be a H-filter. The diffusion extractor may be dimensioned to allow carboxylic acid to diffuse out of the oil sample into a solvent.

The method may comprise detecting of the extracted carboxylic acid by spectrometry. The carboxylic acid may be naphthenic acid. The microfluidic system may be a low Reynolds number fluidic system.

Embodiments of the eighth aspect of the invention may include one or more features of any of the first to seventh aspects of the invention or their embodiments, or vice versa.

According to a ninth aspect of the invention, there is provided a method of detecting the presence and/or level of asphaltene in a lubricating oil sample comprising providing a microfluidic system comprising:
  a microfluidic device comprising at least one microchannel; and
  a detector device;
  passing a lubricating oil sample through the at least one microchannel;
  detecting the presence and/or level of asphaltene in the sample.

The method may comprise extracting, separating and/or diffusing carboxylic acids from the oil sample before detecting the presence of and/or measuring the level of the carboxylic acid.

The method may comprise measuring a first component of the oil sample which may be used to infer or determine the presence or measurement level of asphaltene. The first component may be asphaltene-free fraction such as maltene fraction, of the oil.

The method may comprise passing the sample through a H-filter. The H-filter may be dimensioned to allow asphaltene-free fraction to diffuse out of the oil sample into a solvent and asphaltene to remain.

The method may comprise performing spectra readings of asphaltene-free fraction and the whole oil. The method may comprise determining the presence or quantification of asphaltene by analysing the difference between the spectra readings of asphaltene-free fraction and the whole oil.

Embodiments of the ninth aspect of the invention may include one or more features of any of the first to eighth aspects of the invention or their embodiments, or vice versa.

According to a tenth aspect of the invention, there is provided a method of detecting the presence and/or level of sulphur in a lubricating oil sample comprising providing a microfluidic system comprising:
- a microfluidic device comprising at least one microchannel; and
- a detector device;
- passing a lubricating oil sample through the at least one microchannel;
- detecting the presence and/or level of sulphur in the sample.

The method may comprise extracting, separating and/or diffusing sulphur from the oil sample before detecting the presence of and/or measuring the level of the sulphur.

The method may comprise exposing sulphur present in sample to chemical indicators and/or chemical reagents located in the at least one microchannel.

The method may comprise chemically immobilising and/or reacting the sulphur present in sample to the chemical indicators and/or solid chemical reagents located in the at least one microchannel.

The method may comprise detecting a signal. The signal may be a marking or tarnishing on the surface of the metal detectable by a camera, microscope and/or other inbuilt sensor including those operating in the infrared.

The method may comprise increasing the temperature of the sample to promote a reaction. This may be required if there is no elemental sulphur present in the sample.

Embodiments of the tenth aspect of the invention may include one or more features of any of the first to ninth aspects of the invention or their embodiments, or vice versa.

According to an eleventh aspect of the invention, there is provided a method of detecting the presence and/or level of detergency or alkaline reserve in a lubricating oil sample the method comprising:
- providing a microfluidic system comprising:
- a microfluidic device comprising at least one microchannel;
- and a detector device;
- passing a lubricating oil sample through the at least one microchannel;
- detecting the presence and/or level of detergency in the sample.

The method may comprise extracting, separating and/or diffusing phenolates, sulphonates and phosphonates of alkaline and alkaline-earth elements e.g. calcium (Ca), magnesium (Mg), sodium (Na) or Ba (barium) salts, from the oil sample before detecting the presence of and/or measuring the level of the alkaline reserve or detergency.

The method may comprise measuring a first component of the oil sample which may be used to infer or determine the presence or measurement level of detergency or alkaline reserve.

The first component may be additives of the oil such as phenolates, sulphonates and phosphonates of alkaline and alkaline-earth elements e.g. calcium (Ca), magnesium (Mg), sodium (Na) or Ba (barium) salts.

The method may comprise passing the sample through a diffusion extractor. The diffusion extractor may be dimensioned to allow alkaline additives to diffuse out of the oil sample into a toluene solvent. The method may comprise performing spectra readings of alkaline additives. The method may comprise determining the presence or quantification of the alkaline reserve of the oil by analysing the difference between the spectra readings of alkaline additives n-alkane and the whole oil.

Embodiments of the eleventh aspect of the invention may include one or more features of any of the first to tenth aspects of the invention or their embodiments, or vice versa.

According to a twelfth aspect of the invention there is provided a microfluidic chip for a microfluidic system, the microfluidic chip comprising at least one microchannel configured to allow a sample of lubricating oil to pass therethrough.

Embodiments of the twelfth aspect of the invention may include one or more features of any of the first to eleventh aspects of the invention or their embodiments, or vice versa.

According to a thirteenth aspect of the invention, there is provided a method of detecting the presence and/or level of n-alkane insolubles in a lubricating oil sample comprising providing a microfluidic system comprising:
- a microfluidic device comprising at least one microchannel; and
- a detector device;
- passing a lubricating oil sample through the at least one microchannel;
- detecting the presence and/or level of n-alkane insolubles in the sample.

The method may comprise measuring a first component of the oil sample which may be used to infer or determine the presence or measurement level of n-alkane insolubles. The first component may be n-alkane insolubles-free fraction such as maltene fraction, of the oil.

The method may comprise passing the sample through a diffusion extractor. The diffusion extractor may be a H-filter. The diffusion extractor may be dimensioned to allow n-alkane insolubles-free fraction to diffuse out of the oil sample into a solvent and n-alkane insolubles to remain.

The method may comprise performing spectra readings of n-alkane insolubles-free fraction and the whole oil. The method may comprise determining the presence or quantification of n-alkane insolubles by analysing the difference between the spectra readings of n-alkane insolubles-free fraction and the whole oil.

The n-alkane insolubles may be selected from the group comprising asphaltene, soot, organic solids and/or wear/abrasion products.

Embodiments of the thirteenth aspect of the invention may include one or more features of any of the first to twelfth aspects of the invention or their embodiments, or vice versa.

According to a thirteenth aspect of the invention, there is provided a microfluidic system for monitoring the condition of lubricating oil comprising:
- a microfluidic device comprising at least one microchannel configured to allow a sample of lubricating oil to pass therethrough as a laminar flow; and
- at least one separating device configured to separate at least one component from the lubricating oil in the fluid flow; wherein the microfluidic system comprises a detector device configured to detect the presence and/or measure at least one property of the at least one component passing through the microfluidic device after separation in the microchannel.

Embodiments of the fourteenth aspect of the invention may include one or more features of any of the first to thirteenth aspects of the invention or their embodiments, or vice versa.

BRIEF DESCRIPTION OF THE DRAWINGS

There will now be described, by way of example only, various embodiments of the invention with reference to the drawings, of which:

FIG. 1A is a schematic exploded view of a microfluidic system in accordance with a first embodiment of the invention;

FIGS. 1B to 1D are side and plan views of the assembled microfluidic system of FIG. 1A;

DETAILED DESCRIPTION

Figure 1C:
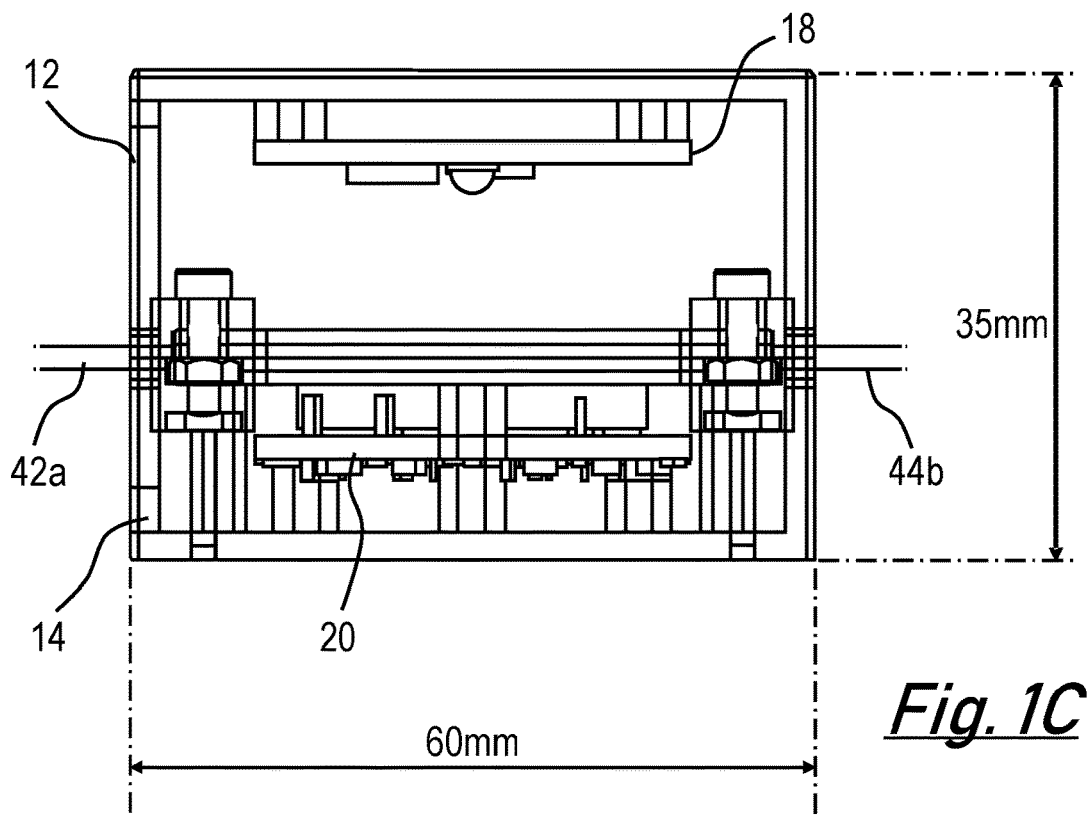
Figure 1D:
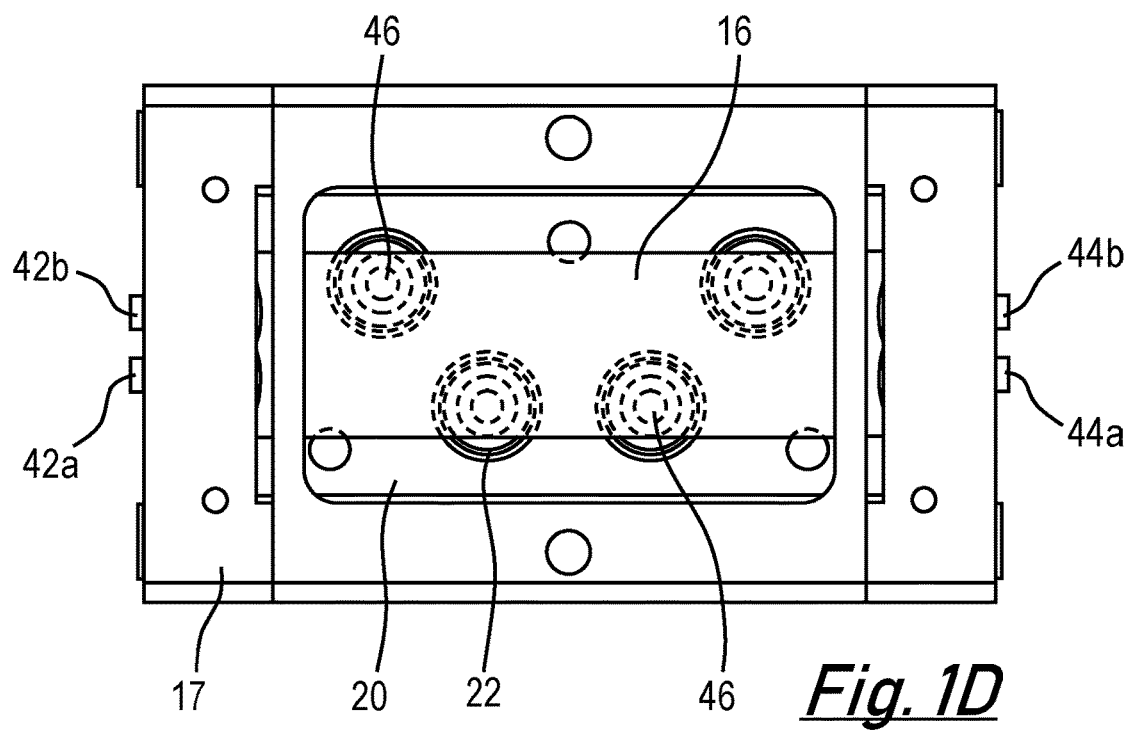

Referring firstly to FIGS. 1A to 1D, there is shown a microfluidic system 10 for monitoring the condition of lubricating oil. The microfluidic system is a low Reynolds number fluidic system.

The system 10 comprises an upper casing 12 and a lower casing 14. In FIG. 1B the upper casing and a lower casing have been removed for clarity. The upper and lower casing when assembled house a microfluidic chip 16, a microfluidic chip support 17, a LED printed circuit board assembly 18 and a detector printed circuit board assembly 20.

The LED assembly 18 consists of five narrowband LEDs (not shown). In this example the five narrowband LEDs have wavelengths of 255 nm, 310 nm, 340 nm, 365 nm and 390 nm respectively. However, it will be appreciated that light sources emitting a wavelength in the range of 200 nm to 890 nm may be used. The detector assembly 20 has four broadband detectors 22. In this example the detectors are photodetectors in combination with the LEDs with suitable optical filter that act as a spectrometer.

The microfluidic chip 16 has a microchannels 40 connected to fluid inlets 42a, 42b and fluid outlets 44a, 44b. The microfluidic chip 16 has observation sites 46. The four detectors 22 sit directly below four observation sites 46 on the microfluidic chip 16. The LED assembly 18 and five LEDs are positioned above the microfluidic chip 16 as shown in FIGS. 1B and 1C.

In use, each one of the LEDs are switched on one at a time. A spectroscopy reading from the narrow band receiver from each observation sites for each of the five LEDs of different wavelengths, this provides twenty readings per sample. The sample rate can be adjusted depending on the resolution required, for example this could be twenty readings every second.

Oil samples and solvents are introduced into the microfluidic chip 16 using pumps (not shown) connected to the inlets 42a and 42b. The injection processes may be automated to control volumetric flow rate and ensure there is optimal diffusive mixing of the oil and extraction solvent in microfluid chip 16.

Figure 2A:
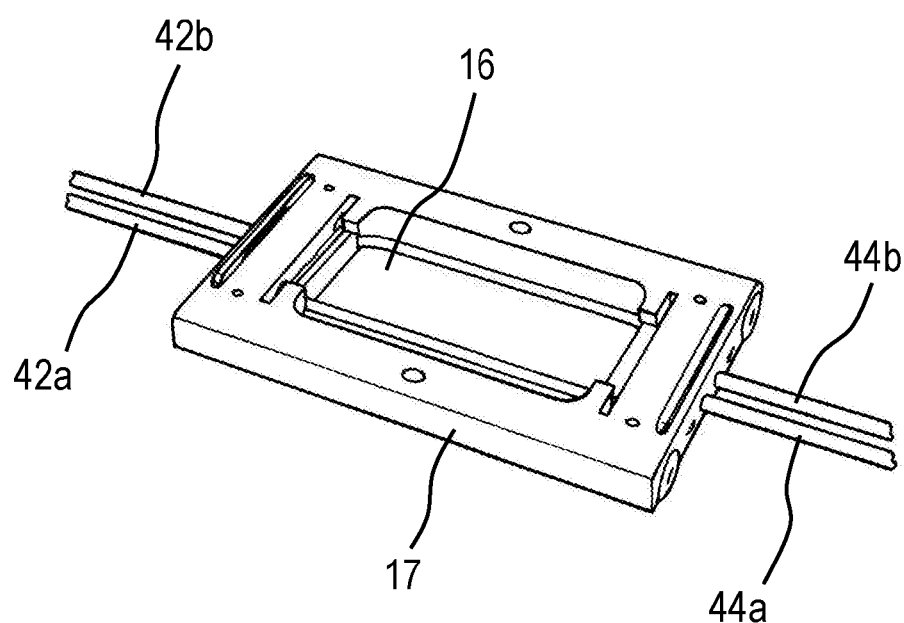
FIG. 2A is a schematic perspective view of the microfluidic chip support and microfluidic chip of the microfluid system of FIG. 1A.
Figure 2B:
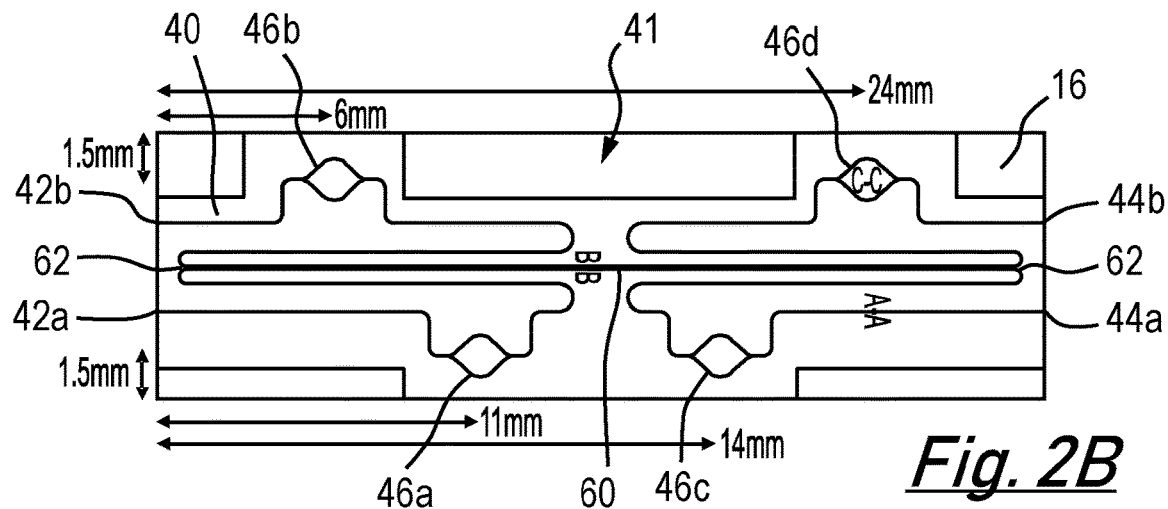
FIG. 2B is a schematic plan view of the microfluidic chip of FIG. 2A, the microfluidic chip support has been removed for clarity.
Figure 2C:
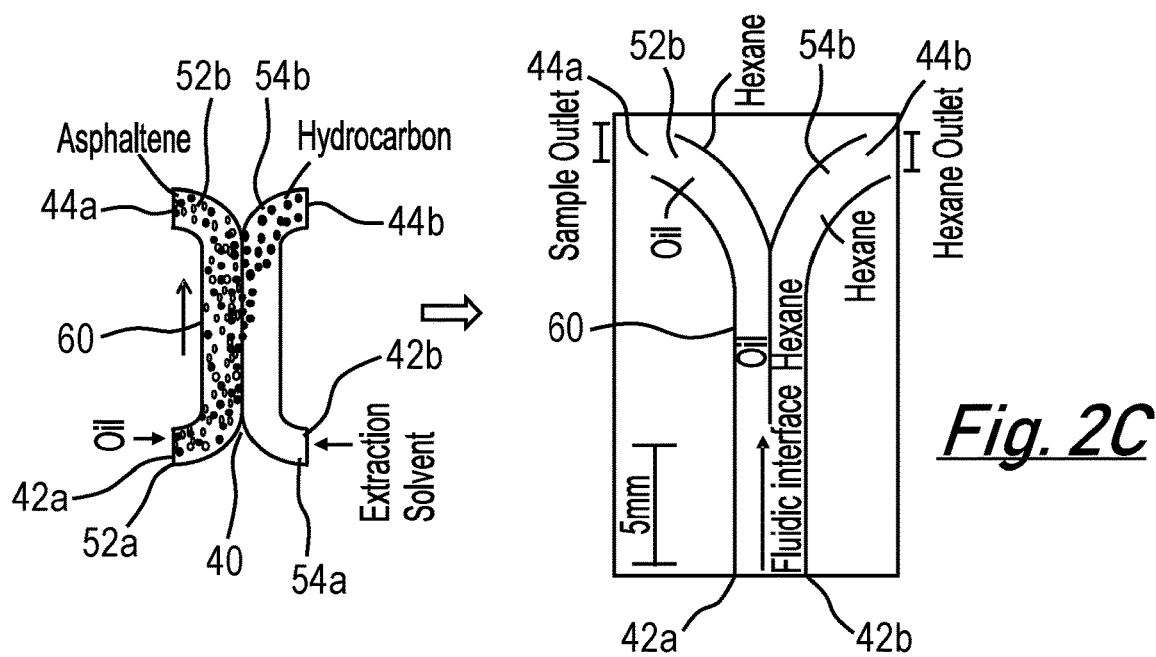
FIG. 2C is a schematic enlarged plan view of the microchannel of microfluidic chip of FIG. 2A.

The microchannels 40 have a diffusion extractor which in this example is a H-filter 41 arrangement best shown in FIG. 2B. As shown in FIGS. 2B and 2C in the microchannels, fluid flow is usually linear-laminar and the surface to volume ratio of fluids is increased so that surface forces (capillary and interfacial forces) dominate fluid flow. Laminar flow is characterised by a low Reynolds number which is the ratio of interfacial forces to viscous forces. In the microfluidic device, the Reynolds numbers are kept below 1000 or below 100 or below 10 or particularly below 1.

In the diffusion extractor 41 as fluid flow is linear-laminar, molecular movement in the fluid stream is parallel, i.e. there is no turbulence. Therefore, mass transfer (i.e. movement of molecules) can occur through convection or diffusion across the fluid interface. This forms the basis of the diffusion extractor operation.

Figure 2D:
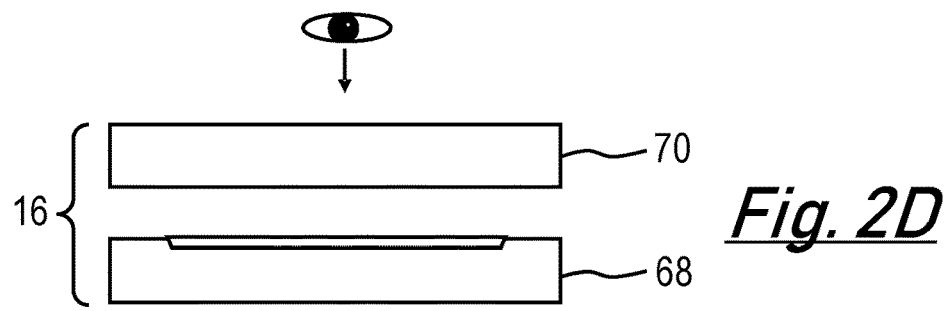
FIG. 2D is an enlarged schematic sectional end view of the microfluidic chip of FIG. 2A.

FIG. 2B shows a microfluidic chip 16 which has microchannels 40 arranged in a diffusion extractor 41. The diffusion extractor 41 has an interface diffusion channel 60 formed the merging of microchannels at a H-junction 62. Four observations wells 46 interrupt the microchannels 40. The diffusion channel 60, Y-junction 62 and observations wells 46 are wet etched onto a 700 μm thick fused silica glass 68 (bottom glass layer). A top 700 μm thick fused silica glass layer 70 is then annealed to the bottom glass layer 68 forming a single 1.5 mm thick microfluidic chip 16. FIG. 2D shows a cross-section view of the microchannel created by the etching process.

As shown in FIG. 2C, a lubricating oil sample 52*a* and a solvent 54*a* are introduced into the diffusion channel 60 via two separate input arms 42*a* and 42*b*. The laminar interface nature of fluid flow within a microfluidic channel 40 ensures molecular diffusion in the diffusion channel 60 is the only way for molecules to move across the fluid interface.

Diffusivity as determined by diffusion coefficients defines the rate of movement of particles within a fluid stream. Small molecules have larger diffusion coefficient thus ensuring they can move quickly through a fluid stream, whereas larger molecules have smaller diffusion coefficients. For example, when hydrocarbons are flowed in contact with a solvent in a microchannel, the first molecules to partition across the interface of both fluid streams will be those with small molecular masses (higher diffusion coefficient). This difference in diffusion coefficients is used to separate molecules over time. As shown in FIG. 2C the solvent and low molecular weight components 54*b* exit the diffusion extractor via outlet 44*b* whereas the remaining particles and high molecular weight components 52*b* of the oil sample exit via outlet 44*a*.

Thus, movement of molecules within the diffusion extractor channel is through diffusion across the parallel fluid interface of the diffusion channel. The time that a particle moving through the microfluidic device has to cross from one fluid stream to another is called the residence time. The residence time is controlled and used to selectively enrich the extracting phase in a chosen compound. Lubricating oil sample introduced into the microfluidic chip is usually diluted and the dilution factor is varied depending on the viscosity of the lubricating oil. Then the ratio of the sample phase to the extracting phase is set so that the solvent and sample occupy an approximately 40:60 share of the channel's width.

In this example the diffusion channel is 260 μm in width "B-B" of FIG. 2B, 28 mm in length and 60 μm in depth. The H-junction has two 130 μm wide channels of 60 μm depth "A-A" of FIG. 2B. The four observation spectroscopy cells 46*a*, 46*b*, 46*c* and 46*d* have diameter dimensions of 1500 μm. The 1.5 mm thick glass chip is 30 mm long and has a breadth of 9 mm "C-C" of FIG. 2B. The dimensions of the diffusion extractor 41 are used to adjust and set the diffusion extractor parameters such as volume, area of channel, wetted perimeter and hydraulic diameter. These parameters are in turn important for the calculation of dimensionless numbers operating within the H-filter.

Reynolds number and capillary number are examples of dimensionless numbers operable in the diffusion extractor 41, both of which characterise flow behaviour of fluid within the diffusion extractor channel.

Table 1 summaries the diffusion extractor dimensions in this example and gives the values for important diffusion extractor parameters.

TABLE 1

Summary of diffusion extractor dimensions

Inner Diameter: 260 μm
Length of Channel: 20 mm (20000 μm)
Width: 130 μm
Depth: 60 μm
Area: 13455.6 μm$^2$ (0.000134556 cm$^2$)
Wet Perimeter: 568.5 μm
Hydraulic Diameter (Dh): 94.7 μm (0.00947 cm)
Channel Volume: 2.69 × 10$^8$ μm$^3$ (0.269 μl)

The Internal volume does not include volume of the inlets 42*a*, 42*b* and outlets 44*a*, 44*b*.

This microfluidic chip 16 is made from fused silica glass material to permit transmittance of light in the wavelength region below 300 nm wavelength range. By wet etching on only one half of the glass layer presents a functionality advantage in that it may eliminate the development of air bubbles which may disrupt stable laminar flow in the microfluidic channel 40.

Example techniques and methods by which the microfluidic system 10 may detect analytes in lubricating oil and measure parameters of the analytes are described in further detail herein.

The operation of the microfluidic device is described in relation to the detection and measurement of four example analytes in lubricating oil which are indicators of wear in machinery and engine components, namely n-alkane insolubles such as asphaltene, carboxylic acid such as naphthenic acid, metal, and sulphur.

Example 1—Detection of n-Alkane Insolubles—Asphaltene

The detection of n-alkane insolubles such as asphaltene in lubricating oil may provide an indication of contamination from fuel derived components such as intermediate or residual fuel oil.

N-alkane insolubles such as asphaltene in lubricating oil may result from the ingress of raw fuel and/or the entry of products of combustion from the sides of piston rings. The ingress of n-alkane insolubles through raw fuel may occur as a result of failure in fuel injector pumps/pump drives and seals in engine ancillaries.

The accurate measurement of n-alkane insolubles in lubricating oil may act as a direct measure of combustion and contamination by residual fuel oil.

The microfluidic system 10 uses the diffusion extractor which in this example is a H-filter 41 arrangement to detect and measure n-alkane insolubles levels in lubricating oil samples. This allows detection of low proportions of n-alkane insolubles in used lubricating oil.

For n-alkane insolubles quantification, spectra readings of asphaltene-free fraction and whole oil are obtained when the sample in the observation sites is exposed to different wavelengths of the individual LEDs on the LED assembly. The data is combined and spliced.

Figure 3:
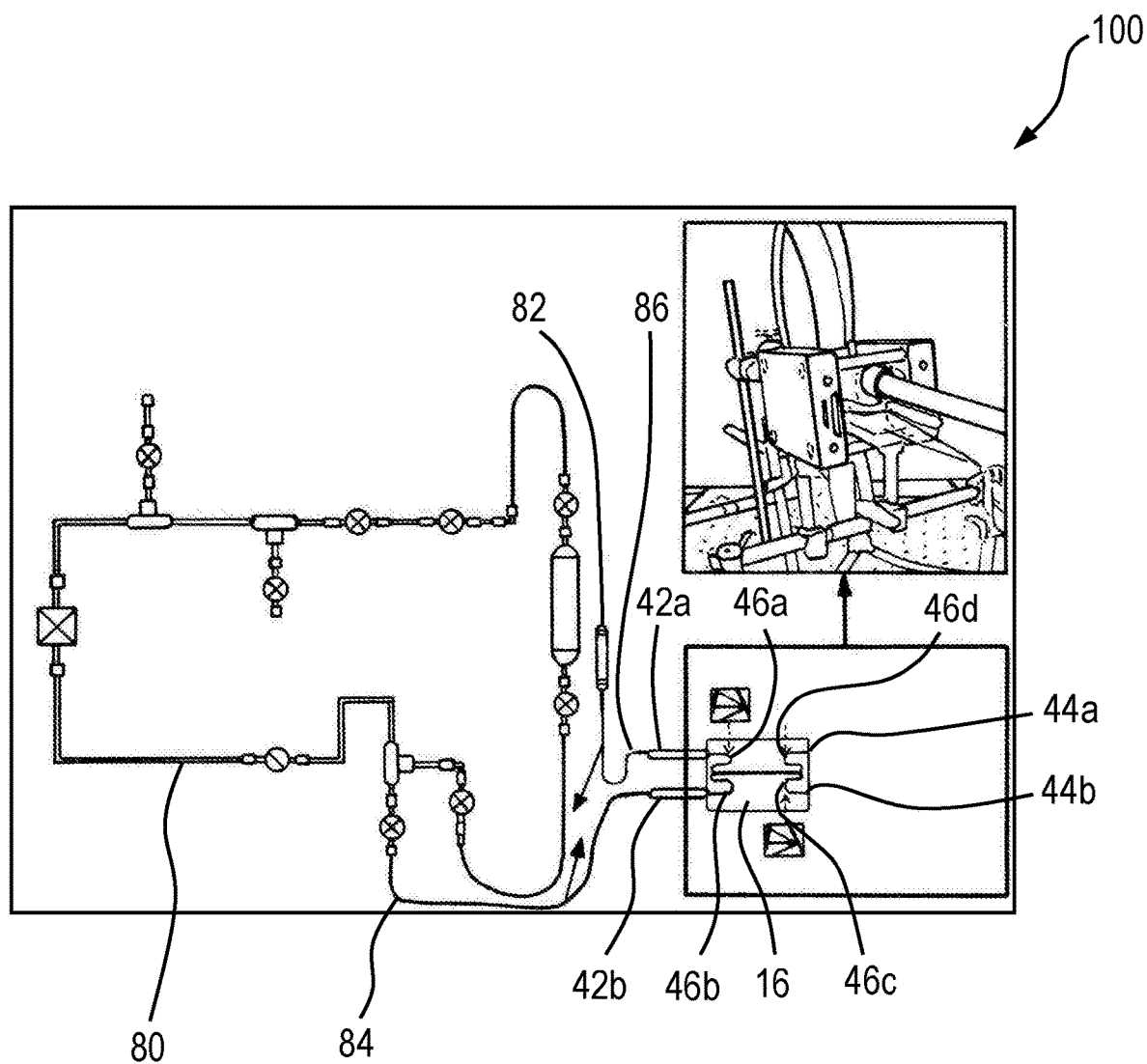
FIG. 3 is a schematic perspective view of a microfluidic system in accordance with an embodiment of the invention.

FIG. 3 presents the experimental set-up used to quantify the proportion of n-alkane insolubles in lubricating oil samples. The system 100 includes a pressure pump system 80. The pressure pump system 80 is connected to inlet 42*b* on the microfluidic chip by tubing 84. A metered dispensing system 82 is connected to inlet 42*a* on the microfluidic chip by tubing 86. In this experiment the syringe 82 simulates a by-pass system from a piece of machinery. A spectroscopy unit including a UV-Vis light source and detector is connected to the microfluidic chip.

The pressure pump system 80 is actuated to pump extraction solvent, in this example hexane into the microfluidic chip via inlet 42b. The metered dispensing system 82 is actuated to pump lubricating oil into the microfluidic chip via inlet 42a. The injected oil and hexane solvent first fill observation sites 46a and 46b located in the inlet channels 42a and 42b respectively in the microfluidic chip before the fluids entering into the diffusion channel 60 in the diffusion extractor channel 41. The fluids then fill observation sites 46d and 46c at output channel 44a and 44b before the fluids exit the microfluidic chip. The Reynolds number is kept below one to ensure that fluid flow is linear and laminar, i.e. there is no turbulent-mixing between sample and solvent. The microfluidic chip is a low Reynolds number fluidic chip. In other application the Reynolds numbers may be kept below 1000 or below 100 or below 10 or particularly below 1.

In this example, the microfluidic chip is positioned in a holder firmly attached to a breadboard. Fibre optic cables were affixed above and below the spectroscopy cells by means of 3D printed hoods and held in place by rods from the breadboard. The fibre optic cables located below the spectroscopy cells are connected to a UV-Vis light source 88 while the fibre optic cables located above the spectroscopy cells were connected to a spectrometer detector 90 (Ocean optics USB4000).

Injecting the solvent using the pressured pump system 80 ensures that the solvent stream was continuous. In use on an actual machinery, the oil stream would be the continuous stream. Nevertheless, a closed system solvent stream in this experimental case enabled the assessment of a pulsed free flow system for oil injection where flow within the channel would be sufficiently stable to obtain good spectral data for analysis.

Spectra data was acquired for whole-oil and extracting phases. The spectra data was acquired for whole-oil fluid as it passed through observation site 46a in inlet channel 42a of the microfluidic chip 16. Downstream, at the outlet channel 44a, spectra data was acquired at observation site 46d for the extract after diffusive separation in the diffusion channel of the diffusion extractor.

The extract phase contained some oil but was n-alkane insolubles-free and had a similar spectrum to the de-n-alkane insolubles oil. The spectrometer measured within the wavelength range of 170 to 890 nm or more specifically 200 to 410 nm; in effect, operating the spectrometer as a single-beam spectrometer.

When a sample is introduced to the diffusion extractor 41 as a pulse a situation is created where flow conditions within the diffusion extractor are transient but stable (e.g. the interface between the extracting and samples fluids moves from the solvent to analyte exit channels as the flow rate of the sample phase decreases). In this situation representative spectra can be identified as that which exhibits the greatest spectral difference to the original sample.

The integration time was 500 ms and scans were not averaged because of the need to produce continuous spectra in real time. Spectra were normalised, smoothed and then cropped (290 nm to 410 nm range). The differences between spectra data of the whole oil taken at observation site 46a and the extract reading taken at observation site 46d were used to obtain the proportion of n-alkane insolubles in an oil sample.

Figure 4A:
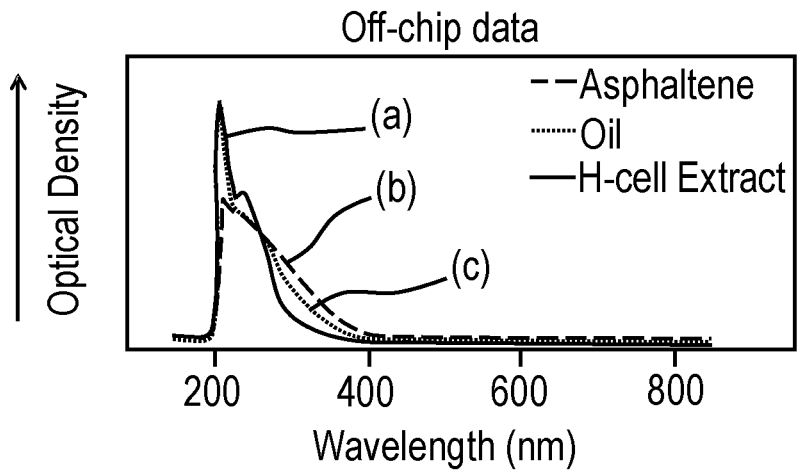
FIG. 4A is a normalised UV-Vis adsorption-spectra for petroleum fractions.

N-alkane insolubles absorb strongly in the 190 to 410 nm range of the UV-Vis spectrum as shown in FIG. 4A line (b). Absorption in this region is less for a conventional non-asphaltic whole-crude line (c) and even less for the maltene fraction (de-n-alkane insolubles oil) line (a).

To determine the n-alkane insolubles content in an oil sample a comparison of the data of n-alkane insolubles spectrum and the maltene fraction was made. The percentage of n-alkane insolubles spectra that is required to restore a maltene fraction spectra to its original whole-oil is used to estimate the n-alkane insolubles content of oil.

Figure 4B:
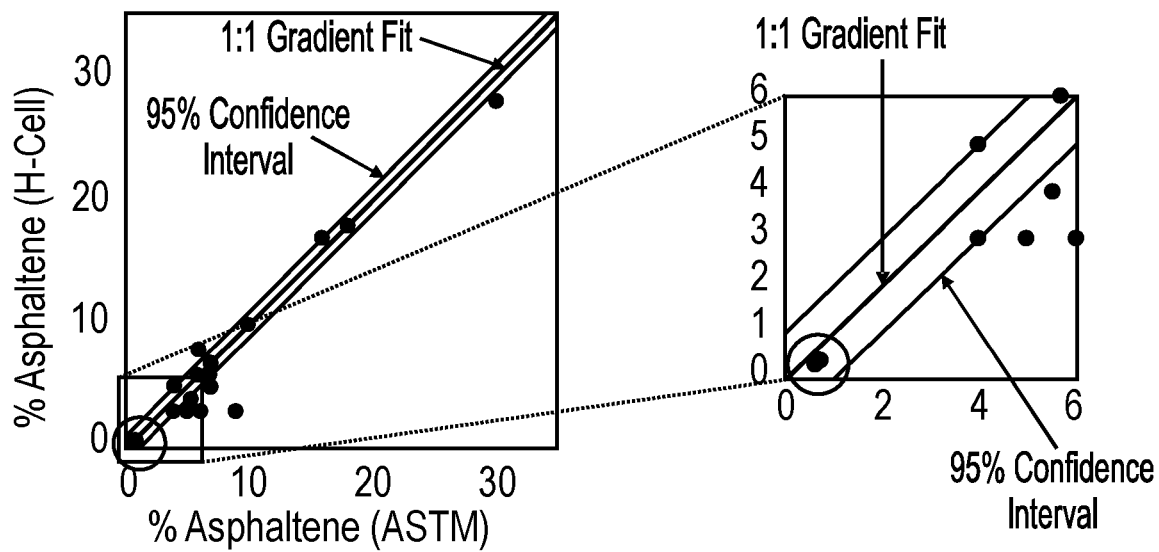
FIG. 4B is a graphical comparison of percentage of n-alkane insolubles-asphaltene predicted by the microfluidic device of FIG. 1A with ASTM (American Society for Testing and Methods) D893.

FIG. 4B shows n-alkane insolubles content values determined from the on-chip analysis for sixteen crude oil samples and two lubricating oil samples are compared to the ASTM (American Society for Testing and Methods) D893 standard method.

FIG. 4B shows that there is a strong correlation in the n-alkane insolubles such as asphaltene values determined by both methods for residence times of 5.6 s. The correlation is significant for an alpha value of 0.001 (r>0.96 and n=18) which suggests that the microfluidic chip analysis is comparable with the ASTM D893 standard.

Thus, a calibration of the standard ASTM D893 method to the microfluidic chip method may be achieved.

FIG. 4B shows that the results appear to closely approximate a 1:1 gradient fit. The two lubricating oils plot are close to the origin of the x and y axis at the lower end of FIG. 4B (the circled two lowest data points). The gravimetric ASTM D893 method determined the n-alkane insolubles content in the main and auxiliary engine oils as 0.7% and 0.6% respectively whilst the diffusion extractor method determined these to be 0.4% and 0.3% respectively.

The ability of the microfluidic chip to rapidly detect low concentrations of n-alkane insolubles such as asphaltene in lubricating oil allows for applications of the system in online, real-time and continuous monitoring of machinery and engines.

Example 2—Detection of Carboxylic Acid

The exposure of lubricating oil to contaminants such as water, air, by-products of combustion (e.g. nitric acid, sulphuric acid) and high temperatures may result in gradual degradation and oxidation of the oil.

The onset of oxidation of lubricating oil triggers a chemical chain reaction in which alkyl radicals formed as the first products of oxidation undergo transformation into peroxy radicals in the presence of oxygen. These peroxy radicals form hydroperoxides and alkyl radicals on further reaction with the oil, creating a chain reaction that accelerates the oxidation process.

As antioxidant additives in formulated lubricating oils are consumed due to oil-aging and exposure to contaminants, the alkaline reserve i.e. basicity of the oil becomes gradually depleted and neutralised by various oxidation by-products.

This increases the acid composition of the oil as strong acids e.g. nitric acid and weak acids such as carboxylic acids i.e. naphthenic acids are increasingly produced. The production of weak acid species such as naphthenic acids is an indication of elevated oxidation conditions in the oil while strong acids signal engine combustion.

A measure of basicity and acidity of an oil is given by Total Base Number (TBN) and Total Acid Number (TAN) respectively. TBN which is a measure of reserve alkalinity of a lubricant is expressed in milligrams of potassium hydroxide (KOH) per gram of oil (ASTM D2896) whereas TAN, is the amount of potassium hydroxide (KOH) in milligrams required to neutralise all of the acid in 1 gram of oil (ASTM D2896). Typically, as TBN in the oil decreases, TAN increases due to alkaline detergents continued reaction with acidic by-products from oil oxidation to form more acidic species.

Loss of antioxidants and acid contamination usually impacts corrosiveness and oil viscosity. This causes a loss in the performance and subsequent failure of the lubricating oil.

Figure 12A:
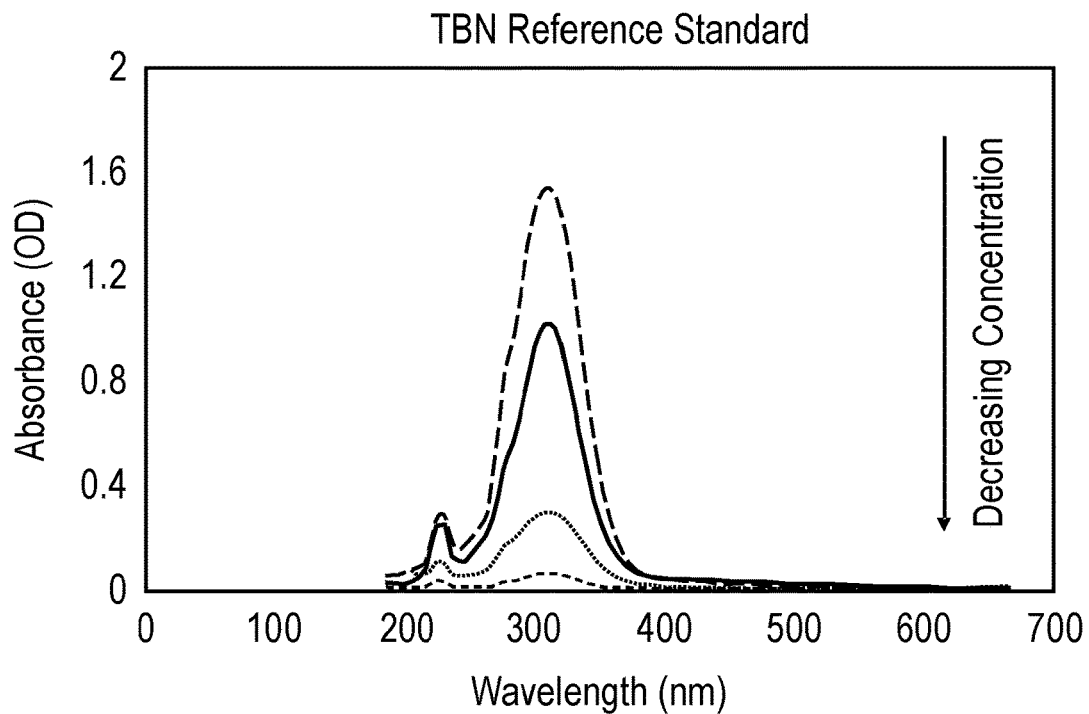
FIG. 12A is a graph showing the spectra of reducing concentrations of TBN reference standard 70 mg KOH/g.

FIG. 12A shows an absorption spectra graph of reducing concentrations (direction of arrow) of TBN reference standard 70 mg KOH/g. As shown in FIG. 12A TBN 70 mg KOH/g has a strong spectral absorption in the UV wavelength region of 200-400 nm.

Figure 12B:
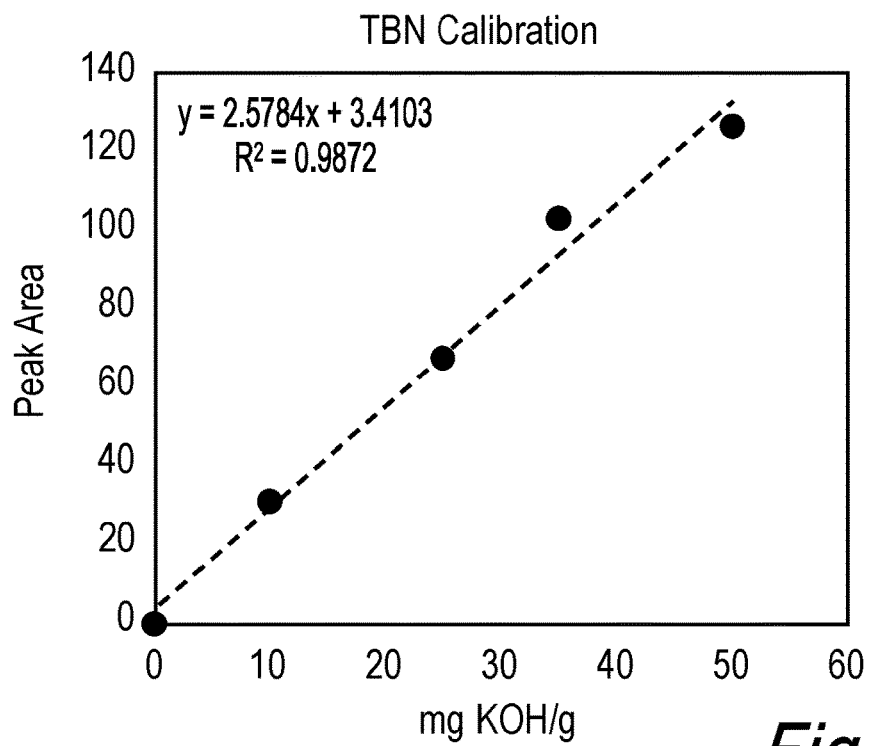
FIG. 12B is calibration graph comparing peak area of reducing concentrations TBN reference standard 70 mg KOH/g.

FIG. 12B shows a calibration graph comparing peak area with reducing concentrations TBN reference standard 70 mg KOH/g. The graph shows that the area of spectra reduces as the concentration of KOH reduces. The graph shows a significantly high correlation between area and reducing concentration of the reference standard. The equation in this graph and shown below is used to calculate the TBN of a sample of lubricating oil with unknown TBN value.

$$y=2.5784x+3.4103$$

$$R^2=0.9872$$

The microfluidic system 10 is configured to detect carboxylic acids molecules in the lubricating oil sample and by extension TAN in lubricating oils. In this example naphthenic acid is detected.

The experimental setup used in detecting naphthenic acids is similar to the setup used to detect n-alkane insolubles as described above in Example 1. The set-up will be understood from the above description in reference to FIG. 3. The system includes a pressure pump system. The pressure pump system is connected to inlet on the microfluidic chip by tubing. A metered dispensing system is connected to inlet on the microfluidic chip by tubing. In this experiment the syringe 82 simulates a by-pass system from a piece of machinery.

However, in this example, a single LED light source transmitting in 250-260 nm wavelength range was used instead of the UV-Vis light source used for n-alkane insolubles quantification in Example 1. The following subsections further describe the experimental set-up, spectral acquisition and processing as well as naphthenic acid quantification.

Similarly, to Example 1, the pressure pump system is actuated to pump methanol (extraction solvent) into the microfluidic chip via inlet 42b.

The metered dispensing system 82 is actuated to pump lubricating oil into the microfluidic chip via inlet 42a. The injected oil and hexane solvent first fill observation sites 46a and 46b located in the inlet channels 42a and 42b respectively in the microfluidic chip before the fluids entering into the diffusion channel 60 in the diffusion extractor channel 41. The fluids then fill observation sites 46d and 46c at output channel 44a and 44b before they exit the microfluidic chip. The Reynolds number is kept below one to ensure that fluid flow is linear and laminar, i.e. there is no turbulent-mixing between sample and solvent. Reynolds numbers are kept below 1000 or below 100 or below 10 or particularly below 1. In this example the metered dispensing system is a hand controlled syringe, however it will be appreciated other dispensing means may be used.

In this example, the microfluidic device is positioned in a holder firmly attached to a breadboard. Fibre optic cables were affixed above and below the spectroscopy cells by means of 3D printed hoods and held in place by rods from the breadboard. The fibre optic cables located below the spectroscopy cells are connected to a LED light source transmitting in 250-260 nm wavelength range while the fibre optic cables located above the spectroscopy cells were connected to a spectrometer detector (Ocean optics USB4000).

Injecting the methanol solvent using the pressured pump system ensures that the solvent stream was continuous. In use on an actual machinery, the oil stream would be the continuous stream. Nevertheless, a continuous solvent stream in this experimental case enabled the assessment of a pulsed flow system for oil injection where flow within the channel would be sufficiently stable to obtain good spectral data for analysis.

In this example methanol is used as the solvent for naphthenic acid determination because it can dissolve organic acids. Additionally, it has a minimum peak wavelength absorbance at 200 nm and is thus effective for naphthenic acids whose absorbance in the low wavelength can range from 205-265 nm. However, other solvents may be used.

UV-Vis absorption spectra were obtained for diffusion extractor methanol extracts using the spectrometer measuring within the wavelength range of 170-890 nm, in effect, operating the spectrometer as a single-beam spectrometer.

The integration time was 500 ms and scans were not averaged because of the need to produce continuous spectra in real time. Spectra were only obtained downstream, at the outlet spectrometry wells. Spectra were acquired for the extract after diffusive separation in the diffusion channel. Spectra were averaged and smoothed.

Figure 5A:
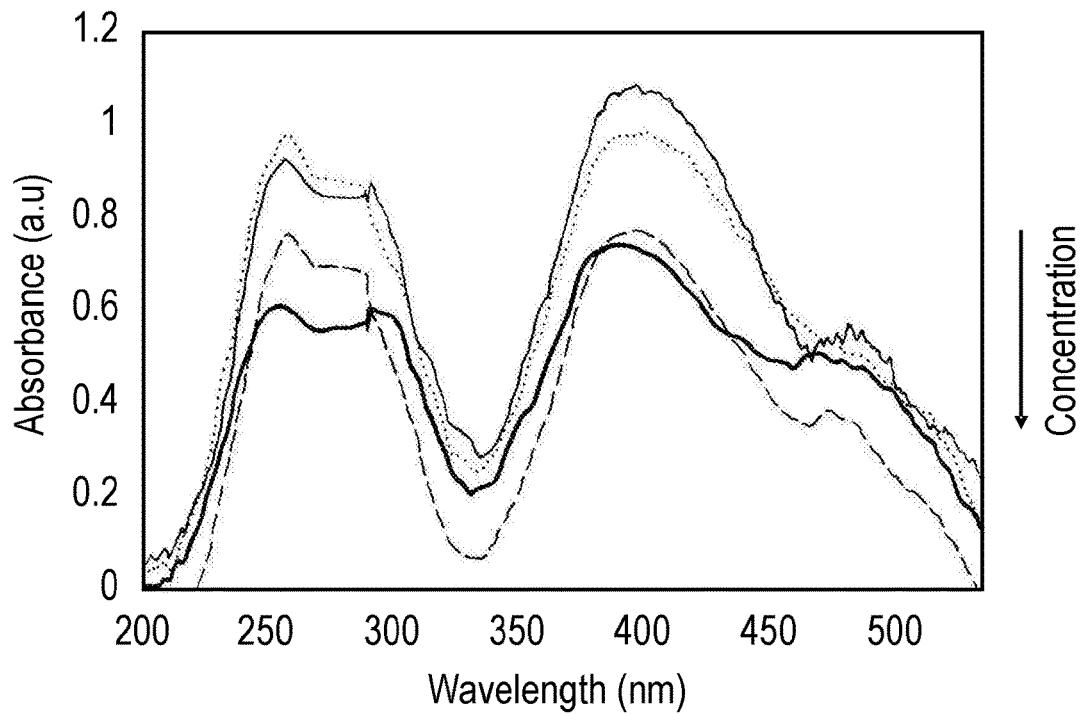
FIG. 5A is an absorption spectra for reducing concentration (direction of arrow) of carboxylic acid-naphthenic acid.

The maximum intensity for absorption of naphthenic acid solutes was at 255 nm wavelength as shown in FIG. 5A. Absorption spectra were acquired for decreasing concentrations of a reference standard—5β-cholanic acid (5 mg/ml) using a series of five progressive 1:10 dilutions. Using absorption in this range a calibration curve was created for the 5γ-cholanic acid standard shown in FIG. 5B.

Oil samples were also processed using Ion Exchange Chromatography—Solid Phase Extraction (IEC-SPE). Analysis was performed using UV-Vis spectroscopy and yielded maximum absorption at 255 nm and a calibration curve was also created.

For naphthenic acid quantification, a calibration curve was used. Acid fractions of two lubricating oil and five crude oil samples were extracted using IEC-SPE, then nitrogen dried, and their weights determined. The proportion of acid fraction was obtained by re-diluting nitrogen-dried acid fraction extracts with 1 ml of methanol. Concentration is obtained using the formula:

concentration=mass/volume(μg/ml)

Figure 5B:
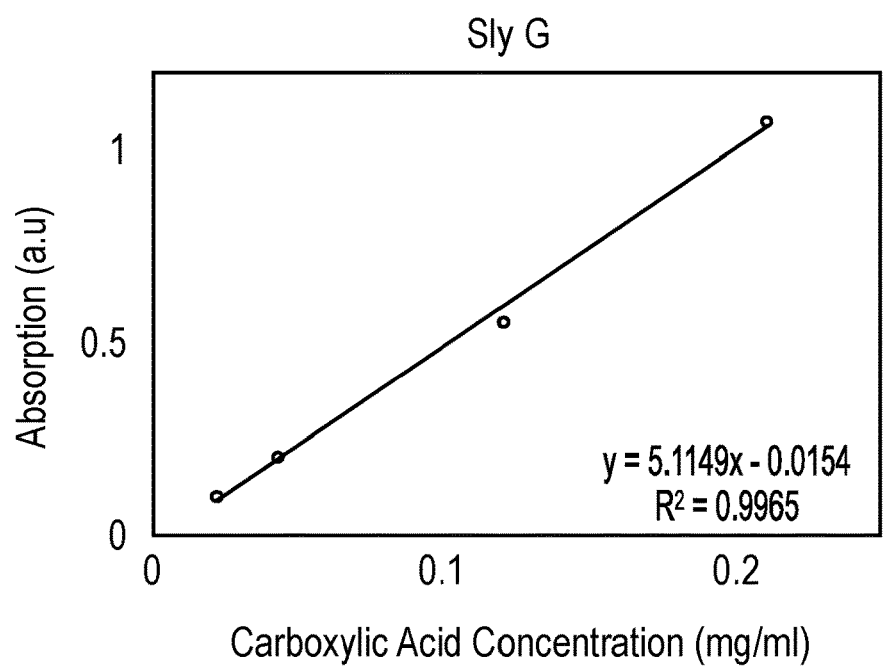
FIG. 5B is a calibration curve of carboxylic acid-naphthenic acid concentration against maximum absorption band peaks.

Known concentrations of acid fraction extracts for all seven samples were then diluted using a 1:10 increasing dilution factor. Spectroscopy data were then acquired for these reduced concentrations and a calibration curve was plotted for peak height against acid fraction concentration. FIG. 5B shows the calibration curve of a lubricating oil sample—main engine oil using this protocol.

For the seven samples, UV-Vis adsorption spectra were acquired, and both the spectra and calibration curves were similar to the naphthenic acid standards. Acid concentrations in methanol extracts were derived from the calibration equations obtained for the standards. The concentration of acid in a given volume of an extract from the low Reynolds number fluidic chip Diffusion extractor was back calculated to obtain the amount of acid present in the volume of oil processed. To do this, the acid fraction yield from the volume of methanol extract obtained was compared to the acid fraction expected to be in the volume of oil processed.

Figure 5C:
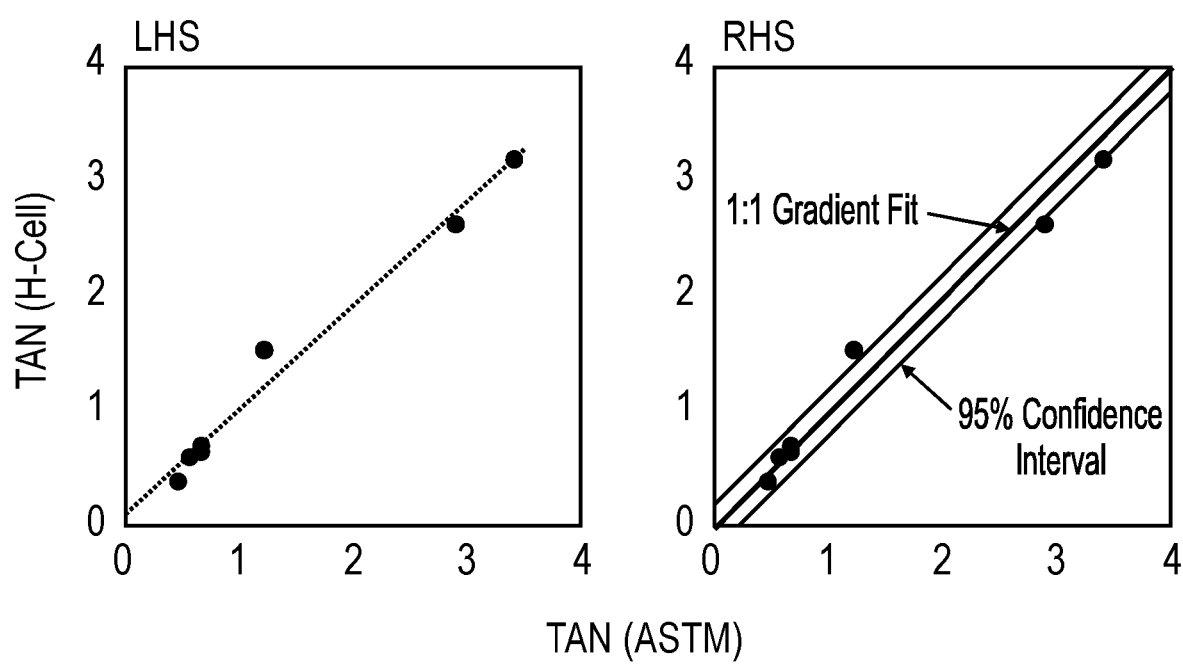
FIG. 5C is a graph of carboxylic acid-naphthenic acid data using the microfluid system according to an embodiment of the invention compared with ASTM D974 method.

FIG. 5C presents a comparison of TAN values obtained using the microfluid system 10 with TAN values obtained via the standard ASTM D974-97.

The TAN data determined via the microfluidic system 10 has the same sequence as those determined via ASTM D974-97 e.g. the most acidic sample determined via ASTM D974-97 corresponds with the most acidic sample according to the microfluid apparatus 10.

The correlation between the TAN values determined by conventional wet chemistry of the ASTM D974-97 and microfluid system, at the diffusion extractor residence optimum time of 5.6 s using methanol as extraction solvent, were significant indicating that the different methods are comparable (significant for an alpha value of 0.001, r=0.99 and n=7). The results appear to closely approximate a 1:1 gradient-fit. Thus, a calibration of the standard ASTM method to the microfluid system 10 may be achieved. Based on intercepts of straight-lines (dashed lines in FIG. 5C) fitted to the data, the detection limit is ~0.01 mg of potassium hydroxide per gram of oil.

The ability of the microfluidic chip to rapidly detect (e.g. below 300 s) naphthenic acid in lubricating oil allows for applications of the system in online, real-time and continuous monitoring of machinery and engines. This has advantages over typical methods of measuring basicity and acidity of oil such as pH sensors have a slow response and low stability are unsuitable for use.

Example 3—Conductivity

Quantitative analysis of trace metals in used lubricating oil may be performed to determine particulate-metal contamination for example metals including Aluminium, Iron, Chromium, Nickel and Tin are of interest in quantitative analysis from a wear and contamination A sudden increase in Chromium, Nickel or Tin concentrations in the lubricating oil may indicate corrosion in bearings, pistons and valves. These metallic particulates may enter lubricating oil during the wearing and abrasion of oil-wetted surfaces. Such particulates range in size from 100 nm-100 μm, and if undetected contribute further to abrasion, erosion and deterioration of component-surfaces.

Metals such as copper can further act as catalyst of oxidation processes further increasing oxidative degradation of the lubricant. Determining the concentration of metallic debris in used-lubricating oil gives an indication of the degree of component wear.

The microfluidic apparatus 310 may detect and quantify nanometre sized metallic debris in used lubricating oil using conductivity and capacitance.

The electrical conductivity of ferrous metals in oil is measured by exposing oil passing through microfluidic apparatus to an electric current or use a high voltage source and a spark plug with varying gaps and measure the breakdown voltage.

Figure 6A:
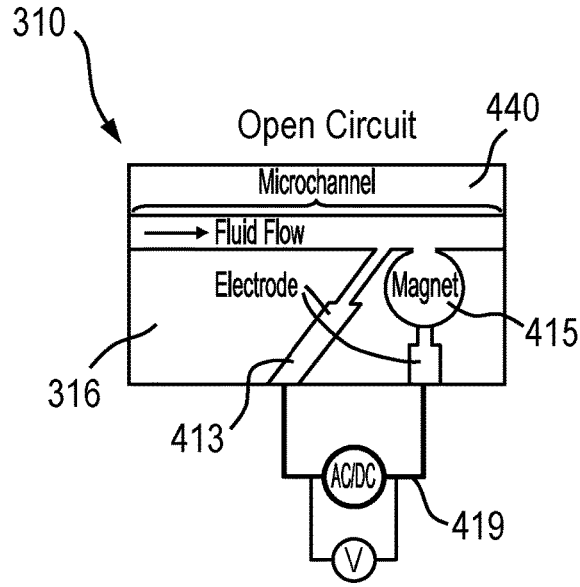
FIGS. 6A and 6B are schematic enlarged sectional views of a microchannel of a microfluidic chip in accordance with an embodiment of the invention.

FIGS. 6A and 6A show enlarged sectional views of the microfluidic chip 416 of the microfluidic apparatus 410. Two electrodes (413, 415) are positioned in or adjacent to microchannel 440 on the microfluidic chip 416. In an open circuit state as shown in FIG. 6A, there is no connection between the two electrodes 413, 415 and no readings are taken.

Figure 6B:
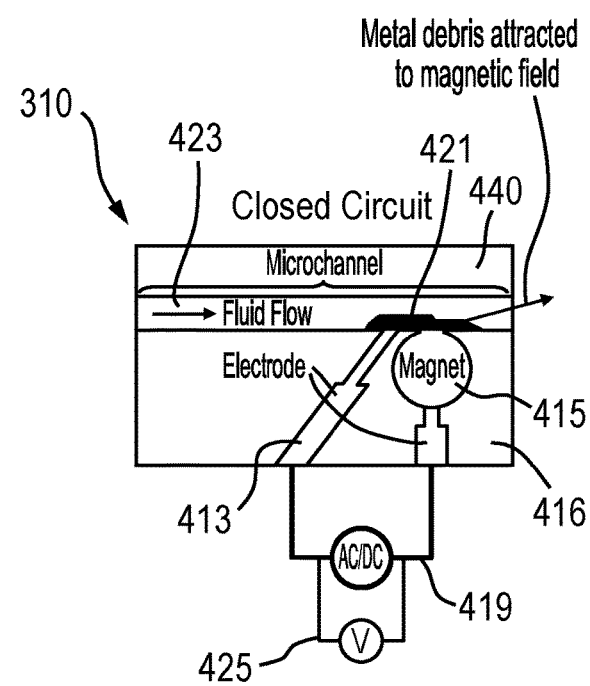

An electrical circuit is created when an electrical source 419 is connected to the two electrodes 413, 415 on the microfluidic device as shown in FIG. 6B. In this example, a permanent neodymium magnet 413 (5 mm diameter×4 mmA-N42-NiCuNi plated permanent neodymium magnet with 0.75 kg pull) acts as a positive electrode 413 to attract ferrous metal debris 421 in the oil 423 extracting or separating them from the fluid flow and forming a connection with the second electrode 415, in this case a copper wire as a negative electrode 415 and thus creating a closed electrical circuit.

The electrodes 413, 415 are connected to an electronic board USB micro-B connector 425 delivering a 20 mA direct current output and generating independent voltages between 0 and 10 V. The potential difference (voltage) across the electrodes can be measured when the circuit is closed, i.e. when a charge is flowing through. The voltage output from the circuit is read off via an electronic board displayed on a computer using a USB micro-B connector.

To measure conductivity, new and used Mobilgard ADL 40 lubricating oil samples were obtained from a Shipping vessel. 0.5 ml of used lubricating oil was spiked with four different masses of 100 nm sized activated-Fe—Ni alloy metal standard. The mass of the 100 nm sized Fe—Ni alloy metal particles was doubled progressively to give four different masses. 1 ml volume of this solution is then introduced into the microfluidic microchannel 440 using a glass pipette.

When oil laden with metallic debris is passed through the microchannel 440, the neodymium magnets 413 attracts the ferrous metals 421 within the oil 423 creating a closed circuit which then gives a voltage reading. Voltage output reduces with reducing concentration of metal in the oil.

Figure 6C:
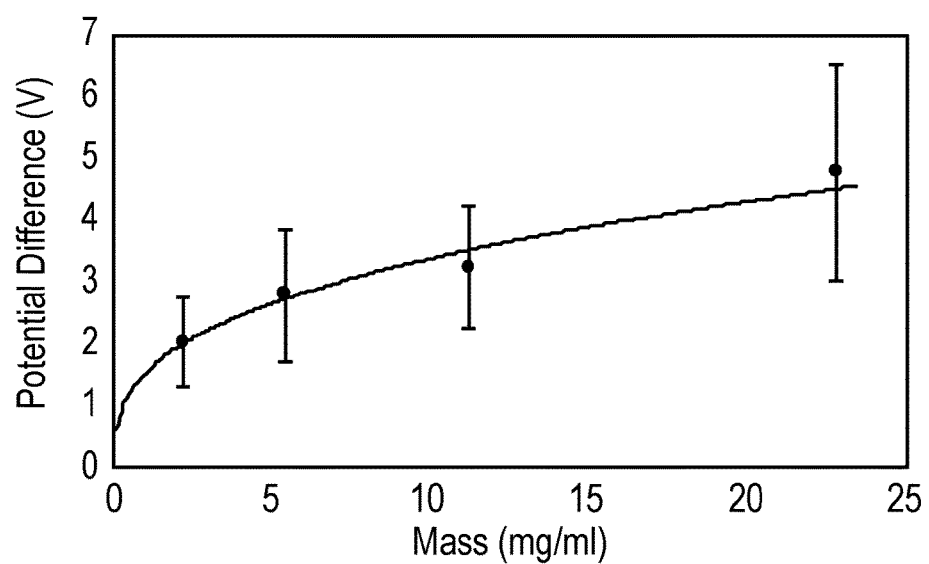
FIG. 6C is a graph representing of mass of Fe—Ni alloy metal particles in lubricating oil plotted against corresponding voltage.

FIG. 6C presents a graph of conductivity measurements in lubricating oil spiked with increasing mass of 100 nm sized Fe—Ni metal particles. A relatively high correlation (r=0.99, n=4 which is significant with an alpha value greater than 0.001) was obtained when an increasing mass of metal particles was plotted against corresponding voltage.

Two replicate measurements were taken, and the error bars show the standard deviation in the measurements.

FIG. 6C shows that voltage across the circuit decreases rapidly as the mass of metal particles approach zero. The conductivity appears to plateau at larger concentrations approaching higher voltage values. A greater amount of work is required to move a unit charge through an electric circuit when the mass of the metal that completes the circuit increases.

The microfluidic device may comprise multiple electric circuits and these circuits may be arranged in series with multiple magnets arrayed along a channel wall and the span of the circuit created used to further quantify the amount of metal present.

A further application of this approach is to use the decreased conductivity of oxidised metal surfaces to distinguish corroded and non-corroded metal particles within lubricating.

Example 4—Capacitance

In this example the microfluidic system 510 comprises a capacitance detection system 511. In this example, the side walls of a microchannel 540 of the microfluidic apparatus 510 is lined with two copper plates 527. The copper plates 527 are connected to a capacitance readout/sensing device 529. The copper plates 527 are covered with a layer of insulating polyvinyl chloride (PVC) material 531 to prevent direct contact of oil 523 or metal debris 521 with the copper plates 527.

When oil laden with metal particles flows across the two capacitance plates 527 in the microchannel 540. Due to differences in permittivity of oil and metal particles a change in capacitance is detected by the capacitance readout/sensing device 529.

Figure 7A:
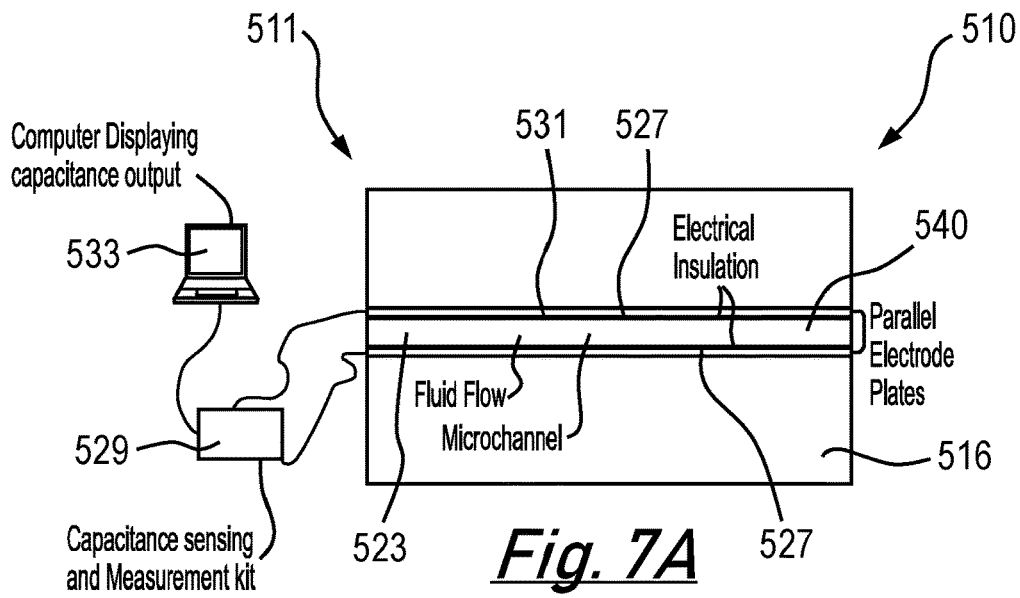
FIGS. 7A to 7C are schematic enlarged views of a microchannel of the microfluidic chip in accordance with an embodiment of the invention.
Figure 7B:
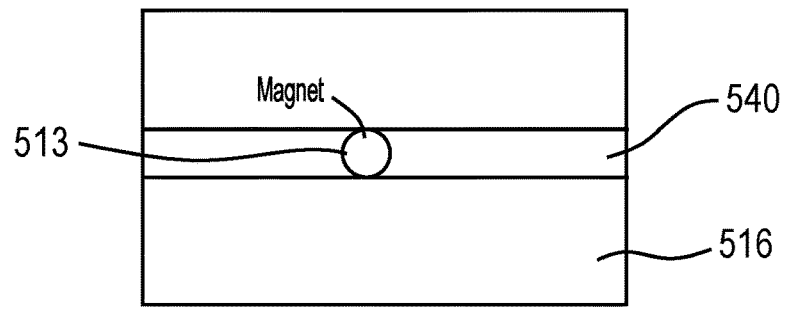
Figure 7C:
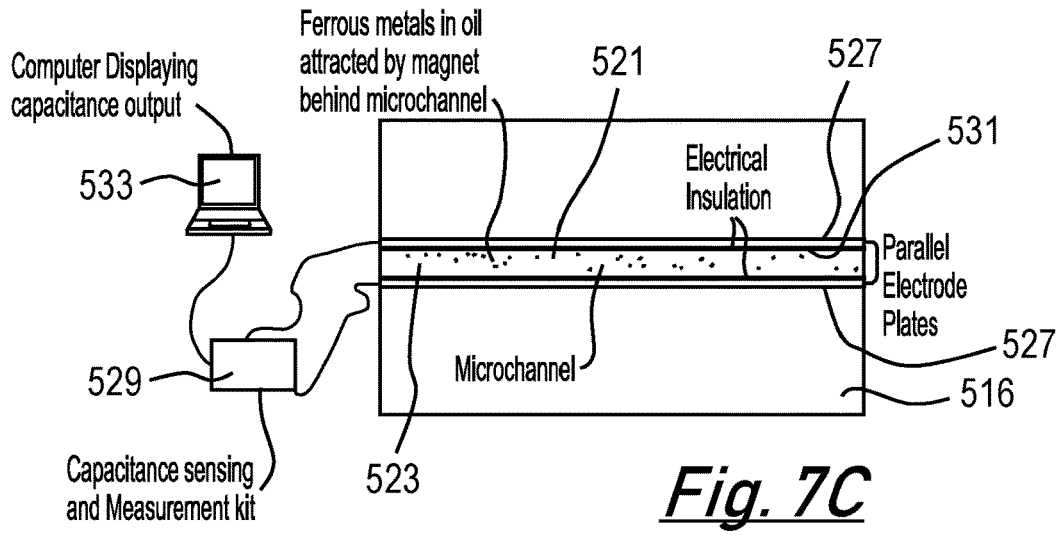

FIG. 7A to 7C shows an enlarged sections of a microfluidic chip 516 setup to measure metal particles in lubricating oil by capacitance. In this example, the microfluidic chip is 3D printed from a Poly Lactic Acid (PLA).

A capacitance circuit 517 is set up by placing two parallel capacitive plates 527 on either side of a microchannel 5 the microfluidic chip. In this example the capacitive plates are 23×3 mm long and the microchannel has a width of 2000 µm.

The plates 527 are electrically insulated with a polyvinyl chloride (PVC) insulation tape 531 to prevent direct electrical conductivity between the plates 527, i.e. short circuiting. In this example the PVC insulation tape is 0.13 mm thick. A NiCuNi plated permanent neodymium magnet 513 (4 mm diameter×2 mmA—N42 with a 0.36 kg pull) is placed directly on the reverse of the fluidic microchannel 540 as shown in FIG. 7B to attract the ferrous metal particles in the oil 523. This also increases the sensitivity of capacitance reading.

The capacitive plates 527 are connected to a capacitive sensing kit which is used to detect a change in capacitance. The capacitance is detected in the picofarad range with attoFrad resolution. The capacitance output in PicoFarad is displayed on a computer by a capacitance readout software.

When oil laden with metal particles passes through the microchannel microfluidic chip the magnet attached to the base of the microchannel (on the reverse side) attracts metal filings and increases the sensitivity of capacitance measurements. A capacitance reading is taken.

Five concentrations of metal in oil were created by mixing different masses of 100 nm sized Iron-Nickel (Fe—Ni) alloy in 5 ml of new lubricating oil. An equal part of toluene was then added to this mix to reduce the oil viscosity.

The samples were injected into the microchannel and a capacitance value was readout from the computer display 533. Three blank capacitance measurement readings were taken for air, toluene, and oil: toluene mix.

Three hundred scans were averaged to produce a capacitance reading per measurement. The test duration for each sample was approximately 20 seconds. Three replicate measurements were taken. The microchannel was cleaned out with toluene, after every sample measurement.

Samples, control and reference materials coded 1-7 are presented in Table 2.

TABLE 2

Result of capacitance measurement of samples

| Sample Code | Sample Name | Concentration (g/ml) | Capacitance (pF) |
|---|---|---|---|
| 1 | Air | | 0.007945 |
| 2 | Oil | | 0.008316 |
| 3 | S0 | 0 | 0.008395 |
| 4 | S1 | 0.005 | 0.008568 |
| 5 | S2 | 0.01 | 0.008649 |
| 6 | S3 | 0.02 | 0.008660 |
| 7 | S4 | 0.04 | 0.008770 |

Figure 7D:
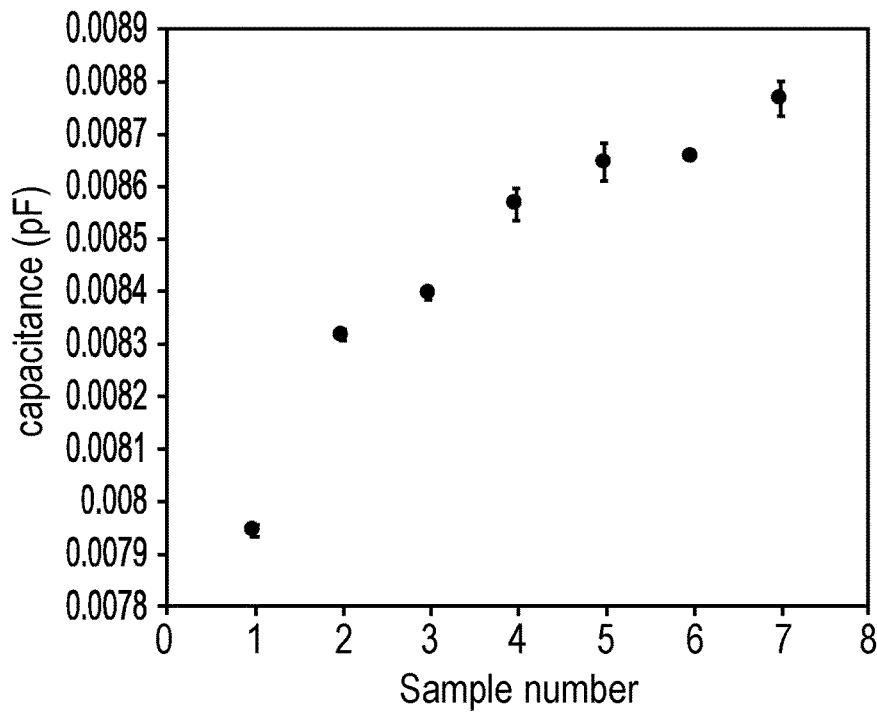
FIG. 7D is a graph representing capacitance measurement from samples of air, toluene, oil and increasing concentrations of metal in oil.

FIG. 7D shows a graph of capacitance reading with increasing concentration of metal in oil. This graph is plotted with sample code on the x-axis and capacitance reading on the y-axis.

The graph shows that capacitance increases with increasing concentration of metal in oil while there are distinctions in capacitance values for air, water and oil lacking any metals.

These results are very repeatable with error bars showing limited deviation from the average following three replicate runs.

At lower concentrations of metal in oil, there is difficulty in distinguishing between the changes in capacitance. This is attributed to the sensitivity of the device. An increase in the gain settings of the measurement device may provide clearer distinction in changes in capacitance with relation to lower metal concentration. This is because changes in capacitance using the capacitance kit can be measured in 10-15 Farad (FemtoFarad) order of magnitude.

The ability of the microfluidic apparatus to detect low concentrations of metal in lubricating oil by capacitance makes it a viable system for monitoring metal wear in machinery and engines.

In the present example, the use of a magnet helps or facilitates the extraction or separation of dispersed metal particles in the oil. By concentrating the metal particles the sensitivity of capacitance reading is increased. By running assays with and without the presence of magnet distinctions can also be drawn between magnetic ferrous metal particulates and non-magnetic particulates (non-ferrous metals).

Additional or alternative steps that may improve the sensitivity of the system include further reducing the width of the microchannel. The unique permittivity of different materials such as air, water, oil etc., makes this capacitance system robust for application across a range of materials. This system presents a rapid low-cost option to more expensive techniques for detecting metals in oil such as ferrography.

Example 5—Incorporation of Chemical Sensors for Sulphur Detection

Sulphur can be present in lubricating oils and machinery in a number of forms. Reactive sulphur species such as sulphides and native sulphur should not be present initially, but may evolve from sulphur species such as salts, dissolved salts within aqueous phases or from intramolecular sulphur found in hydrocarbons such as thiophenes. Sulphur analysis is required in lubricating oils because free sulphur and sulphides can react with metals, fluids and plastics and may cause corrosion. Very low concentrations of sulphur may be produced from both the thermal breakdown of sulphur-containing organic molecules such as thiophenes, or via reduction of dissolved sulphate. The latter can be thermally or biologically mediated. Thus, early and pre-emptive sulphur measurement may not only forewarn of corrosive lubricating oil but also supply information on condition more generally (for example excessive heating).

Standard methods for sulphur detection range from photometric and spectroscopic methods through to mass-spectrometry and gas chromatographs equipped with flame photometric detector, with different methods needed to determine speciation.

In this example the microfluidic apparatus identifies the presence of reactive sulphur species in lubricating oil to indicate corrosion and/or to identify that the breakdown of other sulphur-bearing species has occurred. This provides an indicator of poor-conditions within machinery or engine.

The sulphur and sulphide assays depend on the reaction between metals and sulphur, often within the aqueous phase to determine sulphur concentrations. In this case, reactions occur in non-aqueous phases and at the interface between a fluid and solid. A copper strip test was performed to determine the rate of formation of copper sulphide when native sulphur in discrete fluids of oil and toluene was brought in contact with a copper strip.

Sulphur in discrete oil and toluene mixtures were prepared in reducing concentrations. A sulphur in toluene mixture was prepared by introducing 0.5 g of native sulphur to 30 ml of toluene to form a stock solution of 0.01667 g/ml concentration. Reducing concentrations of sulphur in toluene was created by halving concentrations of the stock solution and resulting solutions thereafter and making it up to the mark with toluene.

Similarly, to prepare a stock solution for sulphur in oil, 1 g of native sulphur was introduced to 30 ml of toluene to form a stock solution with concentration 0.033 g/ml. 0.5 ml of this stock solution was introduced into 0.5 ml of gearbox oil to form a 0.0166 g/ml solution of sulphur in oil. Reducing concentrations of sulphur in oil was then prepared by further dilutions.

Figure 8A:
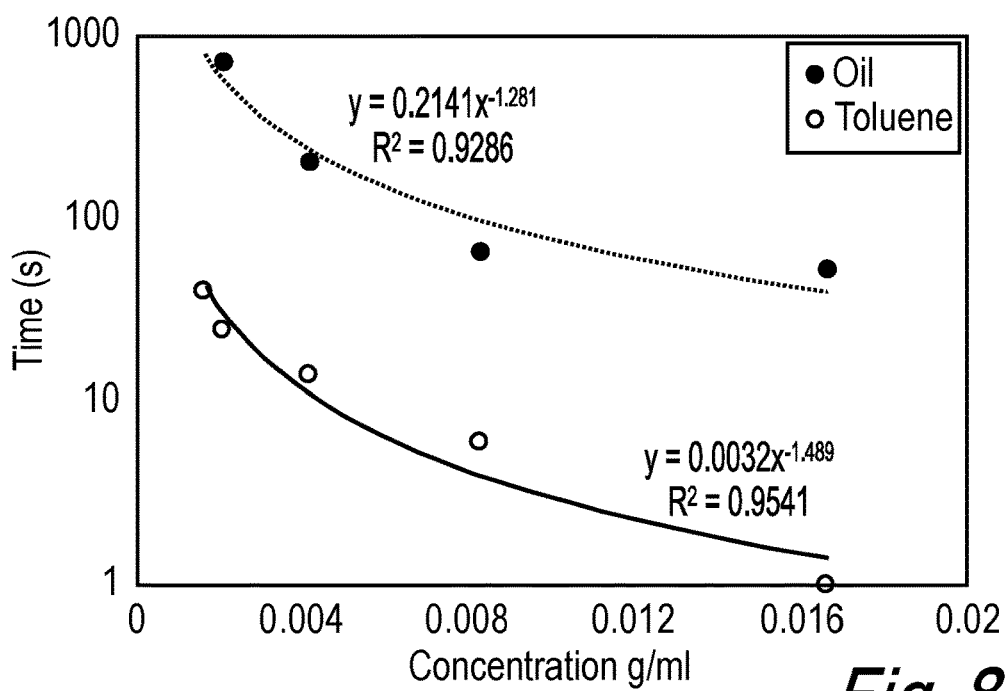
FIG. 8A is graph showing reaction times for the formation of copper sulphide in a reaction of sulphur in oil/toluene with copper, the filled circles represent oil, the empty circles represent toluene.

FIG. 8A presents a graph showing the time required for copper sulphide to formed when a droplet of sulphur in discrete fluids of oil and toluene is introduced to an 8×3 mm copper strip.

Both observable and measurable changes occurred on copper strip surface exposed to reducing concentrations of sulphur in toluene and oil. The formation of metal-sulphide caused the darkening of surface of the copper strip.

The rate of formation of the metal sulphide decreased with decreasing concentration of sulphur. Prior to analysis it was necessary to remove any oxides on the surface of the copper strip by dipping the strip in 0.1 M concentration of hydrochloric acid. The formation of dark coloured copper sulphide was observed with the naked eye and time taken for this change in coloration to occur was recorded with a stopwatch. FIG. 8A shows that a calibration curve of reaction times can be created. The filled circles represent oil mixture data, the empty circles represent toluene mixture data.

Figure 9A:
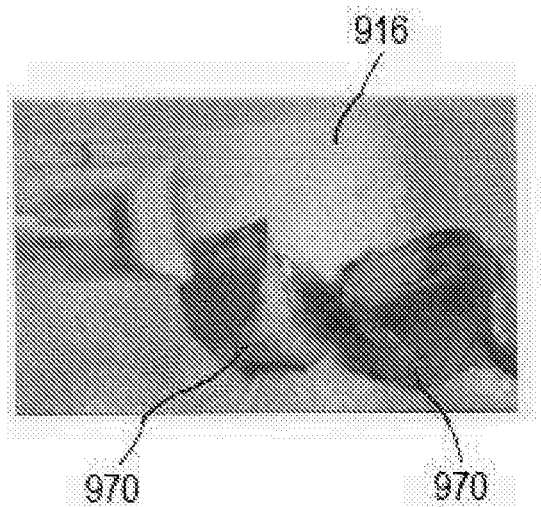
FIGS. 9A and 9B are images of an enlarge view of a microfluidic chip and a glass capillary respectively with embedded silver and copper particles.
Figure 9B:
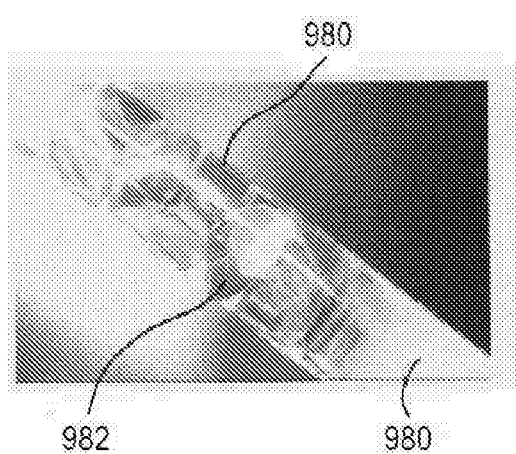

Silver fragments 970 were deposited as discrete components within microchannels of a microfluidic chip 916 as shown in FIG. 9A. Fresh silver surfaces samples were used in the microchannels of a microfluidic chip. Copper fragments 982 were deposited as discrete components within channels of glass capillaries 980 as shown in FIG. 9B. The copper surfaces were activated prior to use, to remove copper oxide from the surface in order to reproducibly bring about changes in colour.

The microfluidic chip and glass capillaries were then exposed to solvent samples containing sulphur.

Figure 10A:
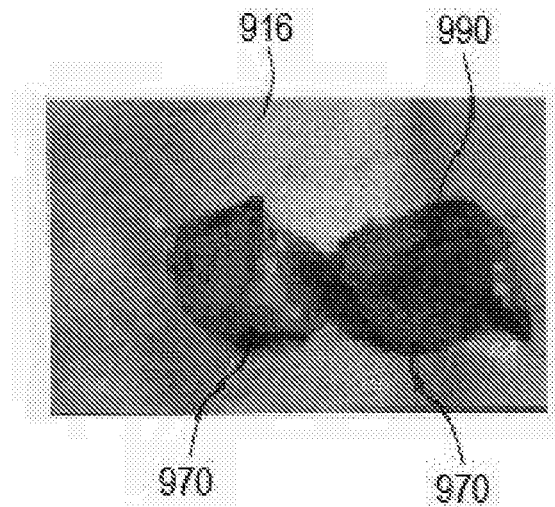
FIGS. 10A and 10B are images of an enlarge view of a microfluidic chip and a glass capillary respectively which show darkening of the silver and copper particles of the particles of FIGS. 9A and 9B respectively.
Figure 10B:
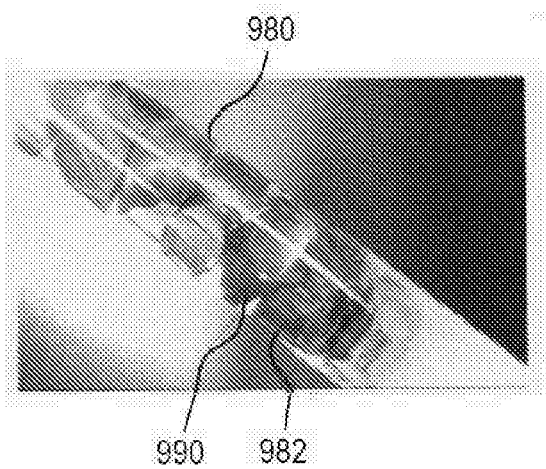

FIGS. 10A and 10B show darkening 990 of the surfaces of the silver fragments 970 and the copper fragments 982 respectively after being exposed to sulphur. The darkening 990 was measured under ambient white light, using a microscope camera and pixel intensity within a given region of interest. The darkening of metal surfaces was used to detect sulphur within the fluids.

Observable and measurable changes occurred on copper and silver metal surfaces exposed to sulphur-saturated toluene and oil. The formation of metal-sulphides on the copper and silver surfaces caused darkening of surfaces. The silver surfaces darkened more quickly than the copper surfaces.

Figure 11A:
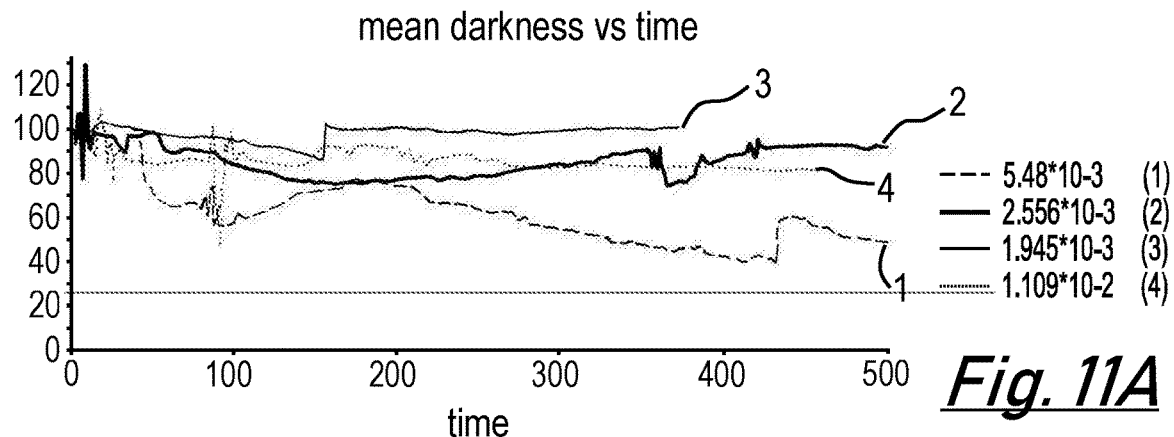
FIG. 11A is a graph of the pixel intensity measured by a microscope camera over time for sulphur darkening.

FIG. 11A show changes observed in pixel intensity over time. From this graph both the depth of change in intensity, as well as the time taken for change to occur can may be used for calibration purposes.

Figure 11B:
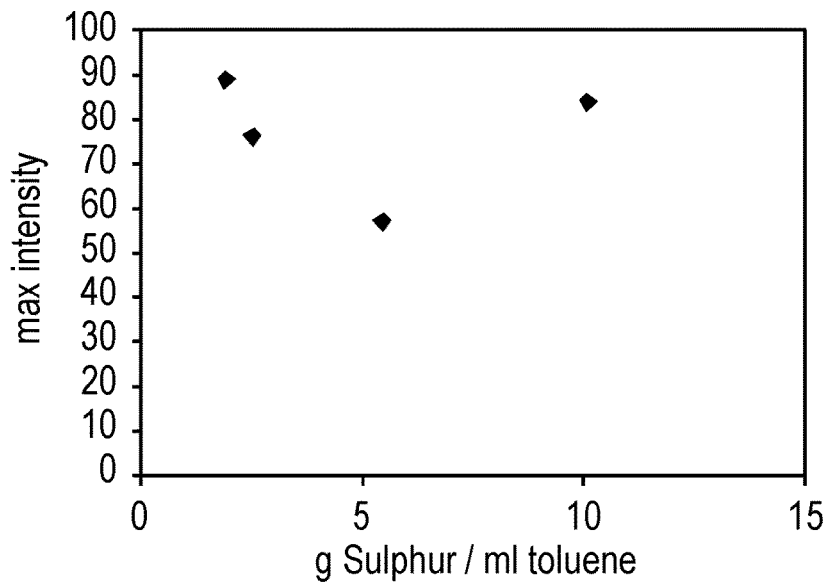
FIGS. 11B and 11C show graphs amount of sulphur vs maximum intensity and time to maximum intensity respectively.
Figure 11C:
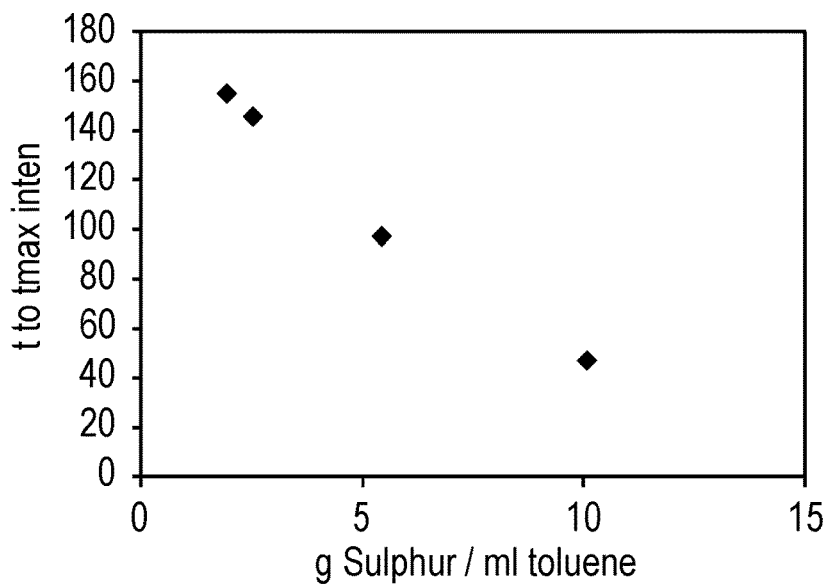
Figure 11D:
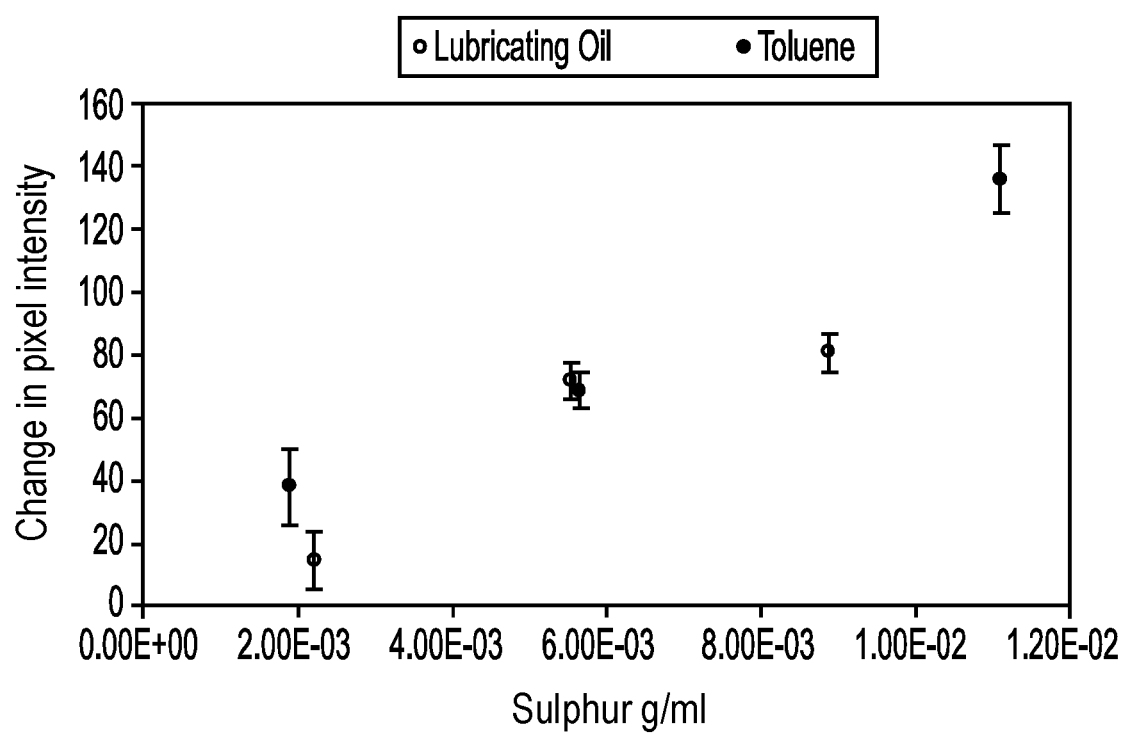
FIG. 11D is a graph showing changes in pixel intensity over time for after circulation of toluene and lubricating oil containing dissolved sulphur.

When applied to sulphur dissolved within oil, it was found that using absolute changes in intensity as shown in FIGS. 11B, 11C and 11D resulted in better reproducibility and generally a lower change in intensity was observed. These graphs show the maximum intensity and time to reach maximum intensity vs amount of sulphur present in the sample. The lower values of the pixel intensity denote darker pixels. For all plots the pixel intensity is the y-scale.

In this example the pixel intensity was measured using the green channel of an RGB image. However, this choice represents only the better operation of the charge coupled device (CCD/CMOS) or another photosensitive device within this range.

Flow rate was slow approximately 25 µl\min for the experiments shown, although constant within an order of magnitude. Flow rate would be expected to become more important at high rates in two respects: 1) the effective increase in surface or concentration achieved and 2) practically because of the dislodging of oxides formed on the surfaces of metals. This latter aspect may responsible for the slightly lesser change in pixel intensity observed for oil experiments compared to toluene experiments, as the later were flushed with toluene to remove oil prior to the measurement of intensity.

In the above example the analyte (sulphur) reactive sensors were embedded as metal fragments within microchannels of the microfluidic apparatus. In alternative embodiments the analyte reactive sensors may be embedded as vacuum deposited surfaces or small solid components. Deployment of analyte (sulphur) reactive sensors such as silver and copper sensor in microchannels to measure dissolved sulphur is practical. By embedding or depositing the metal components in the microchannel the analyte reactive sensors are robust and may be deployed in non-laboratory environments.

In the above example the analyte (sulphur) reactive sensors are single use and are disposable. Repeated use would be facilitated by using replaceable microfluidic chips with a low manufacturing cost. After use, the microfluidic chips may feasibly be recycled, surface regenerated using HCl, or reconditioned.

Additional or alternatively to the CCD\CMOS or another photosensitive device described in the above example, a camera may be used to measure reaction changes. Other optical detection methods such as an infrared sensor may be used.

Such sensors when deployed to autonomously monitor an oil stream can be deployed in a series array with chemical buffers between each sensor. The arrays of sensors may be calibrated and buffered such that the triggering of one sensor within the series acts as a warning that a given concentration of free sulphur has now been reached within the oil, with additional sensors within the array monitoring and characterizing the evolving extent of sulphur contamination in the lubricating oil.

The microfluidic system may be configured to detect and/or measure one or more of metals, carboxylic acid, n-alkane insolubles and/or sulphur at the same time and/or from the same lubricating oil sample.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers. Furthermore, relative terms such as", "inlet", "outlet" and the like are used herein to indicate directions and locations as they apply to the appended drawings and will not be construed as limiting the invention and features thereof to particular arrangements or orientations. The term "outlet" shall be construed as being an opening which, dependent on the direction of the movement of fluid may also serve as an "entry", and vice versa.

The invention provides a microfluidic system for monitoring the condition of lubricating oil comprising a microfluidic device. The microfluidic device comprises at least one microchannel configured to allow a sample of lubricating oil to pass therethrough; and a detector device configured to detect the presence and/or measure the level of at least one analyte in the sample.

The present invention provides a robust, reliable and compact microfluidic apparatus and incorporated chemical and/or physical sensors suitable for monitoring the health and condition of a piece of machinery by analysing the products of wear, degradation and contamination in lubricating oil.

The invention provides a microfluidic chip that is capable of improving the performance of a microfluidic apparatus in which the microfluidic chip is deployed. The microfluidic chip is capable of rapidly detecting and/or measure the level of components in the lubricating oil sample. The microfluidic chip is capable of detecting analytes and/or parameters of analytes in lubricating oil which may be indicative of machinery wear or corrosion and allow high-throughput oil analysis.

The foregoing description of the invention has been presented for the purposes of illustration and description and is not intended to be exhaustive or to limit the invention to the precise form disclosed. The described embodiments were chosen and described in order to best explain the principles of the invention and its practical application to thereby enable others skilled in the art to best utilise the invention in various embodiments and with various modifications as are suited to the particular use contemplated. Therefore, further modifications or improvements may be incorporated without departing from the scope of the invention herein intended.

The invention claimed is:

1. A microfluidic system for monitoring the condition of lubricating oil comprising:
   a microfluidic device comprising at least one microchannel configured to allow a sample of lubricating oil to pass therethrough as a laminar flow; and a
   at least one separating device configured to selectively separate at least one component from the lubricating oil in the fluid flow, wherein the at least one separating device comprises a diffusion extractor configured to allow diffusion across the fluid interface of parallel fluid streams;
   wherein the microfluidic system comprises a detector device configured to detect the presence and/or measure at least one property of the at least one component passing through the microfluidic device after separation in the at least one microchannel.

2. The microfluidic system according to claim 1 wherein the at least one microchannel comprises a plurality of inlets and outlets wherein a first inlet is configured to receive an oil sample and/or a second inlet is configured to receive a solvent.

3. The microfluidic system according to claim 2, wherein the diffusion extractor comprises a diffusion channel and the first inlet and/or second inlet are in fluid communication with the diffusion channel.

4. The microfluidic system according to claim 1 wherein the at least one component from the lubricating oil is selected from the group consisting of metals, carboxylic acid, n-alkane insolubles and/or sulphur.

5. The microfluidic system according to claim 1 wherein the detector device is located in, on, above, below or adjacent to the at least one microchannel.

6. The microfluidic system according to claim 1 comprising at least one observation site.

7. The microfluidic system according to claim 1 comprising a light source.

8. The microfluidic system according to claim 1 wherein the detector device comprises at least one sensor selected from the group consisting of a spectrometer, camera, CCD device, conductivity sensor, capacitance sensor and/or a metal responsive to a chemical analyte.

9. The microfluidic system according to claim 8 wherein the at least one sensor is a spectrometer to detect, measure and/or record a spectrum from the at least one component of the lubricating oil.

10. The microfluidic system according to claim 1 wherein the at least one component is detected or measured by measuring UV-absorption and/or measuring a difference in UV-Vis Absorption.

11. The microfluidic system according to claim 1 wherein the system comprises a second separation device selected from the group consisting of magnet and/or a metal-based sulphur removal device.

12. The microfluidic system according to claim 11 wherein the second separation device is a magnet and the detector device is an electrical conductivity sensor and/or an electrical capacitance sensor.

13. The microfluidic system according to claim 11 wherein the second separation device is a metal-based sulphur removal device selected from the group consisting of copper and silver and the detector device comprises a camera and/or a CCD device.

14. The microfluidic system according to claim 1 wherein the diffusion extractor is a H-filter.

15. The microfluidic system according to claim 1 wherein the detector device is configured to measure a first component of the oil sample which may be used to infer or determine the presence or measurement level of a second component of the oil sample.

16. The microfluidic system according to claim 1, where the at least one microchannel is a diffusion channel or is in fluid communication with a diffusion channel.

17. A method of monitoring the condition of lubricating oil comprising
   providing a microfluidic system comprising:
      a microfluidic device comprising at least one microchannel; and
      at least one separating device, wherein the at least one separating device is a diffusion extractor configured to allow diffusion across the fluid interface of parallel fluid streams; and
      a detector device;
   passing a sample of the lubricating oil through the at least one microchannel in a laminar flow;
   separating at least one component from the lubricating oil in the flow; and
   detecting the presence and/or measuring at least one property of the at least one component passing through the microfluidic device after separation in the at least one microchannel.

18. The method according to claim 17 comprising detecting the presence and/or measuring at least one modal properties of the at least one component in the sample.

19. The method according to claim 17 comprising detecting the presence of and/or measuring the at least one component by spectrometry, electrical conductivity, electrical capacitance and/or reactivity of the at least one component to a chemical indicator.

20. The method according to claim 17 comprising separating with a second separating device the at least one component from the lubricating oil sample by mass transfer, magnetic attraction and/or chemical interaction.

21. The method according to claim 17 comprising taking at least one measurement of the lubricating oil sample before separating the at least one component and comparing with at least one measurement of the sample taken after the at least one component is separated.

22. The method according to claim 17 comprising comparing a spectrum of the lubricating oil sample before separating the at least one component with a spectrum of the extracted at least one component.

23. The method according to claim 17 comprising detecting, measuring and/or recording an electrical capacitance and/or electrical conductivity of the sample after the at least one component is separated or partially separated from the flow.

24. The method according to claim 17 comprising detecting, measuring and/or recording a chemical response of the at least one component to metal sensor and/or metal reagent.

25. The method according to claim 17, wherein the sample of the lubricating oil is a sample of lubricating oil from a piece of equipment, the method further comprising assessing a condition or health of the piece of equipment based on the presence and/or measurement of at least one property of the at least one component from the sample of lubricating oil.

* * * * *